US012471830B2

(12) United States Patent
Patnala et al.

(10) Patent No.: US 12,471,830 B2
(45) Date of Patent: *Nov. 18, 2025

(54) SYSTEMS AND METHODS FOR CALIBRATING SOUND DELIVERY TO A HEARING SYSTEM RECIPIENT

(71) Applicant: Advanced Bionics AG, Staefa (CH)

(72) Inventors: Anil K. Patnala, Stevenson Ranch, CA (US); Kanthaiah Koka, Valencia, CA (US)

(73) Assignee: Advanced Bionics AG, Staefa (CH)

( * ) Notice: Subject to any disclaimer, the term of this patent is extended or adjusted under 35 U.S.C. 154(b) by 0 days.

This patent is subject to a terminal disclaimer.

(21) Appl. No.: 18/743,538

(22) Filed: Jun. 14, 2024

(65) Prior Publication Data

US 2024/0335157 A1 Oct. 10, 2024

Related U.S. Application Data

(63) Continuation of application No. 17/104,908, filed on Nov. 25, 2020, now Pat. No. 12,048,550.

(51) Int. Cl.
*A61B 5/38* (2021.01)
*A61B 5/12* (2006.01)
(Continued)

(52) U.S. Cl.
CPC ................ *A61B 5/38* (2021.01); *A61B 5/125* (2013.01); *A61B 5/24* (2021.01); *A61B 5/291* (2021.01);
(Continued)

(58) Field of Classification Search
CPC ............ H04R 25/505; H04R 2225/025; H04R 25/606; H04R 5/02; H04R 29/001; H04R 25/30; H04R 25/652; H04R 1/345; H04R 9/06; H04R 29/00; H04R 2410/05; H04R 3/00; H04R 1/10; H04R 25/305; H04R 2225/0216; H04R 1/342; H04R 1/1066; H04R 1/406; H04R 1/403; H04R 11/02; H04R 19/016; H04R 19/02; H04R 2400/00; A61B 5/6803; A61B 2562/0204;
(Continued)

(56) References Cited

U.S. PATENT DOCUMENTS 5,999,856 A 12/1999 Kennedy
7,014,613 B2 3/2006 John et al.
(Continued)

*Primary Examiner* — Deborah L Malamud
(74) *Attorney, Agent, or Firm* — ALG Intellectual Property, LLC

(57) ABSTRACT

An illustrative electroacoustic hearing system includes a loudspeaker and a processor configured to: direct the loudspeaker to present a sound to a recipient by way of a length of tubing extending from the loudspeaker to an ear tip disposed at an ear canal of the recipient, the directing configured to cause the sound to have a target sound pressure level at the ear canal; obtain a detected sound pressure level of the sound as the sound is presented at the ear canal, the detected sound pressure level obtained from a probe microphone disposed within the ear tip; identify a discrepancy between the detected and target sound pressure levels of the sound as the sound is presented at the ear canal; and direct, based on the identified discrepancy, a remedial action to be performed to compensate for the discrepancy.

19 Claims, 12 Drawing Sheets

(51) Int. Cl.

| | |
|---|---|
| ***A61B 5/24*** | (2021.01) |
| ***A61B 5/291*** | (2021.01) |
| ***A61N 1/05*** | (2006.01) |
| ***A61N 1/36*** | (2006.01) |
| ***H04R 25/00*** | (2006.01) |

(52) U.S. Cl.

CPC ....... *A61N 1/0541* (2013.01); *A61N 1/36039* (2017.08); *H04R 25/505* (2013.01); *H04R 25/70* (2013.01)

(58) Field of Classification Search

CPC . A61B 5/12; A61B 5/6817; A61B 2562/0247; A61B 5/6815; A61B 5/6816; A61B 5/121; A61B 5/4836; A61N 1/0541; A61N 1/36036; A61N 1/36039; A61N 1/36132; A61N 1/3603; A61N 1/08; A61N 1/00; A61N 1/18; A61N 1/3625; A61N 1/0526

See application file for complete search history.

(56) References Cited

U.S. PATENT DOCUMENTS

| | | | | |
|---|---|---|---|---|
| 8,241,224 | B2 | 8/2012 | Keefe | |
| 9,497,530 | B1 | 11/2016 | Campbell et al. | |
| 10,560,789 | B2 | 2/2020 | Koka et al. | |
| 12,048,550 | B2 * | 7/2024 | Patnala | A61N 1/36039 |
| 2019/0046796 | A1 | 2/2019 | Koka et al. | |

* cited by examiner

SYSTEMS AND METHODS FOR CALIBRATING SOUND DELIVERY TO A HEARING SYSTEM RECIPIENT

RELATED APPLICATIONS

This application is a continuation of U.S. patent application Ser. No. 17/104,908, filed Nov. 25, 2020, which is hereby incorporated by reference in its entirety.

BACKGROUND INFORMATION

Various types of hearing systems are in use today by hearing system recipients with many different hearing capabilities and challenges. For example, people who have little or no natural hearing may benefit from a cochlear implant system that stimulates auditory nerves in ways that natural hearing mechanisms fail to do for various reasons. Certain cochlear implant recipients may also retain partial hearing, such as an ability to hear only certain frequencies. Such recipients may benefit from electroacoustic hearing systems, which may provide both the electrical stimulation of a cochlear implant system (e.g., for certain frequencies) and acoustic stimulation similar to what a hearing aid system would provide (e.g., for other frequencies). Some hearing system recipients may also benefit from use of a bimodal hearing system that employs one type of hearing system (e.g., a standard cochlear implant system) for one ear, and another type of hearing system (e.g., an electroacoustic hearing system, a hearing aid system, etc.) for the other ear.

Regardless of which of these or other types of hearing systems a particular recipient may use, there may be certain situations where it is desirable to present acoustic stimulation (i.e., sound) to the recipient at a carefully-monitored and/or precisely-controlled sound pressure level (e.g., a particular volume level, a specific sound intensity or loudness, etc.). For example, such situations may occur during certain surgical procedures, during clinical fitting sessions or other clinical visits relating to the hearing system, or even during normal operation of certain hearing systems.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

DETAILED DESCRIPTION

Figure 1:
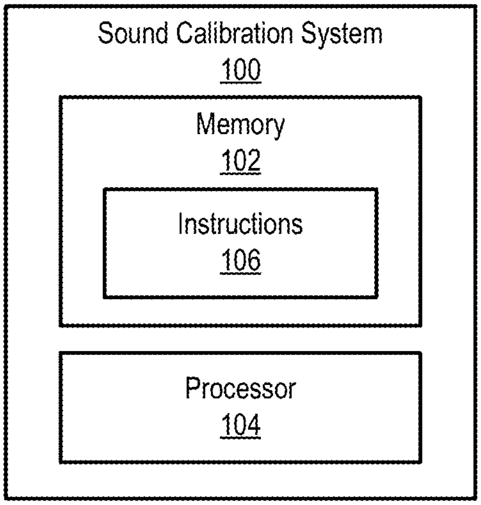
FIG. 1 shows an illustrative sound calibration system configured to calibrate sound delivery to a hearing system recipient.

Systems and methods for calibrating sound delivery to a hearing system recipient are described herein. Delivery of acoustic stimulation, or sound, to a recipient of a hearing system may be performed for various reasons. For example, certain types of hearing systems my deliver sound to recipients during normal operation so as to assist the recipients in perceiving the environment around them. As another example, it may be useful under certain circumstances to deliver sound from a stimulation device directly to an ear canal of the recipient in a precise and controlled manner so as to facilitate proper configuration (e.g., installation, testing, fitting, setup, etc.) of the hearing system. For instance, sound may be presented to evoke involuntary responses (e.g., brain wave potentials and/or other evoked responses) from the recipient during system configuration sessions such as surgical procedures (e.g., electrode lead insertion procedures, etc.), clinical fitting sessions, and so forth.

When sound is presented for these or other purposes, systems and methods described herein may be used to calibrate the sound delivery to be optimally applied, precisely controlled, accurately measured, and/or predictable. To this end, systems and methods described herein for calibrating sound delivery to a hearing system recipient may involve real-time measurements and feedback loops to accurately calibrate sound delivery and ensure that the target sound pressure levels that are supposed to be presented at the ear canal are either actually present or suitably compensated for. For example, along with accounting for known effects that may be expected to affect sound delivery (e.g., length of tubing that carries sound waves, sound leakage, loudspeaker tolerances, etc.), systems and methods described herein help detect and/or compensate for issues that are less predictable and need to be addressed in real-time as the issues arise (e.g., kinks in the tubing that carries the sound waves, blocked ear tips, fluid discharge at the ear canal that affects sound propagation, malfunctioning electronics, etc.).

As used herein, calibration of sound delivery refers to any of the operations, methods, techniques, or the like, that facilitate and/or support the accurate and precise delivery of sound to the ear canal at desired target levels. For example, sound delivery calibration may be performed by any suitable systems or devices described herein, and may involve operations for adjusting and/or otherwise compensating generated sound pressure levels to meet target specifications as indicated by measured sound pressure levels detected at the ear canal. Such corrections and compensations may be performed continuously and in real-time during any system configuration session described herein or under various other circumstances as may serve a particular implementation. In some examples, systems and methods described herein may calibrate sound delivery to a hearing system recipient intraoperatively (e.g., during a surgical procedure), post-operatively (e.g., during a fitting session), and/or in an in-situ manner.

Various benefits and advantages may be provided by systems and methods described herein for calibrating sound delivery to a hearing system recipient. As one illustrative benefit, unanticipated and undesirable issues that arise during a system configuration session (or during normal operation of certain hearing systems) may be addressed and resolved effectively and dynamically such that the issues do not lead to negative or long-lasting consequences as they otherwise might. For instance, if sound delivery tubing gets partially kinked during setup for an electrode lead insertion procedure, it may be difficult or impossible to detect the kink by looking at the tubing (much of which may be carefully taped down for the duration of the surgical procedure), and yet the kink could significantly interfere with acoustically evoked responses that are important for an effective and efficient procedure. Even though it may be difficult to guarantee that no such kink is introduced as a surgical team prepares the recipient for surgery, systems and methods described herein allow for the effects of the kinked tubing (e.g., a reduced sound pressure level at the ear canal compared to the sound pressure level that is targeted by a device generating the acoustic stimulation) to be mitigated and/or compensated for in various ways. For example, a user may be notified to inspect for and fix the kinking, a higher sound pressure level may be introduced to account for the reduction caused by the kinking (e.g., such that the target sound pressure level may still be achieved at the ear canal), the test results may be adjusted, annotated, or reinterpreted to account for the non-optimal sound pressure level that was actually presented (instead of the target sound pressure level that was expected), or the like.

As another illustrative benefit of systems and methods described herein, the sound delivery calibration and consequent correction and/or compensation for detected issues may be performed automatically and dynamically in real time. Systems and methods described herein may also provide peace of mind to surgeons, clinicians, and/or other users associated with the performance of system configuration sessions (e.g., lead insertion surgical procedures, fitting sessions, etc.) due to a reliable indication provided by the system that the sound delivery is fully functional (e.g., there are no kinks, blockages, or other unaccounted for sound delivery issues) prior to commencing with the system configuration session.

Various specific embodiments will now be described in detail with reference to the figures. It will be understood that the specific embodiments described below are provided as non-limiting examples of how various novel and inventive principles may be applied in various situations. Additionally, it will be understood that other examples not explicitly described herein may also be captured by the scope of the claims set forth below. Systems and methods described herein for calibrating sound delivery to a hearing system recipient may provide any of the benefits mentioned above, as well as various additional and/or alternative benefits that will be described and/or made apparent below.

FIG. 1 shows an illustrative sound calibration system 100 ("system 100") configured to calibrate sound delivery to a hearing system recipient in accordance with principles described herein. Sound calibration system may be implemented in various different ways by different hearing system configuration devices (e.g., insertion monitoring devices, clinician fitting devices, etc.) or by different hearing systems (e.g., electroacoustic hearing systems or other cochlear implant systems, bimodal hearing systems, etc.). While certain examples described herein may focus on particular implementations of sound calibration systems, it will be understood that it may be possible for other types of implementations to employ the principles being described (e.g., taking the place of the specific sound calibration system implementations being described or operating in concert with those specific implementations).

System 100 may be implemented by computing resources such as an embedded computing system of a hearing system configuration device, embedded computer resources built into an electroacoustic hearing system processing unit (e.g., a sound processor, etc.), or any other computing resources as may serve a particular implementation. Various implementations of system 100 will be described below.

As illustrated in FIG. 1, system 100 may include, without limitation, a memory 102 and a processor 104 selectively and communicatively coupled to one another. Memory 102 and processor 104 may each include or be implemented by computer hardware that is configured to store and/or execute computer instructions (e.g., software, firmware, etc.). Various other components of computer hardware and/or software not explicitly shown in FIG. 1 may also be included within an implementation of system 100. In some examples, memory 102 and processor 104 may be distributed between multiple devices as may serve a particular implementation.

Memory 102 may store and/or otherwise maintain executable data used by processor 104 to perform any of the functionality described herein. For example, memory 102 may store instructions 106 that may be executed by processor 104. Memory 102 may be implemented by one or more memory or storage devices, including any memory or storage devices described herein, that are configured to store data in a transitory or non-transitory manner. Instructions 106 may be executed by processor 104 to cause system 100 to perform any of the functionality described herein. Instructions 106 may be implemented by any suitable application, software, firmware, script, code, and/or other executable data instance. Additionally, memory 102 may also maintain any other data accessed, managed, used, and/or transmitted by processor 104 in a particular implementation.

Processor 104 may be implemented by one or more computer processing devices, including general purpose processors (e.g., central processing units ("CPUs"), microprocessors, etc.), special purpose processors (e.g., application-specific integrated circuits ("ASICs"), field-programmable gate arrays ("FPGAs"), etc.), or the like. Using processor 104 (e.g., when processor 104 is directed to perform operations represented by instructions 106 stored in memory 102), system 100 may perform functions associated with calibrating sound delivery to a hearing system recipient as described herein and/or as may serve a particular implementation.

Figure 2:
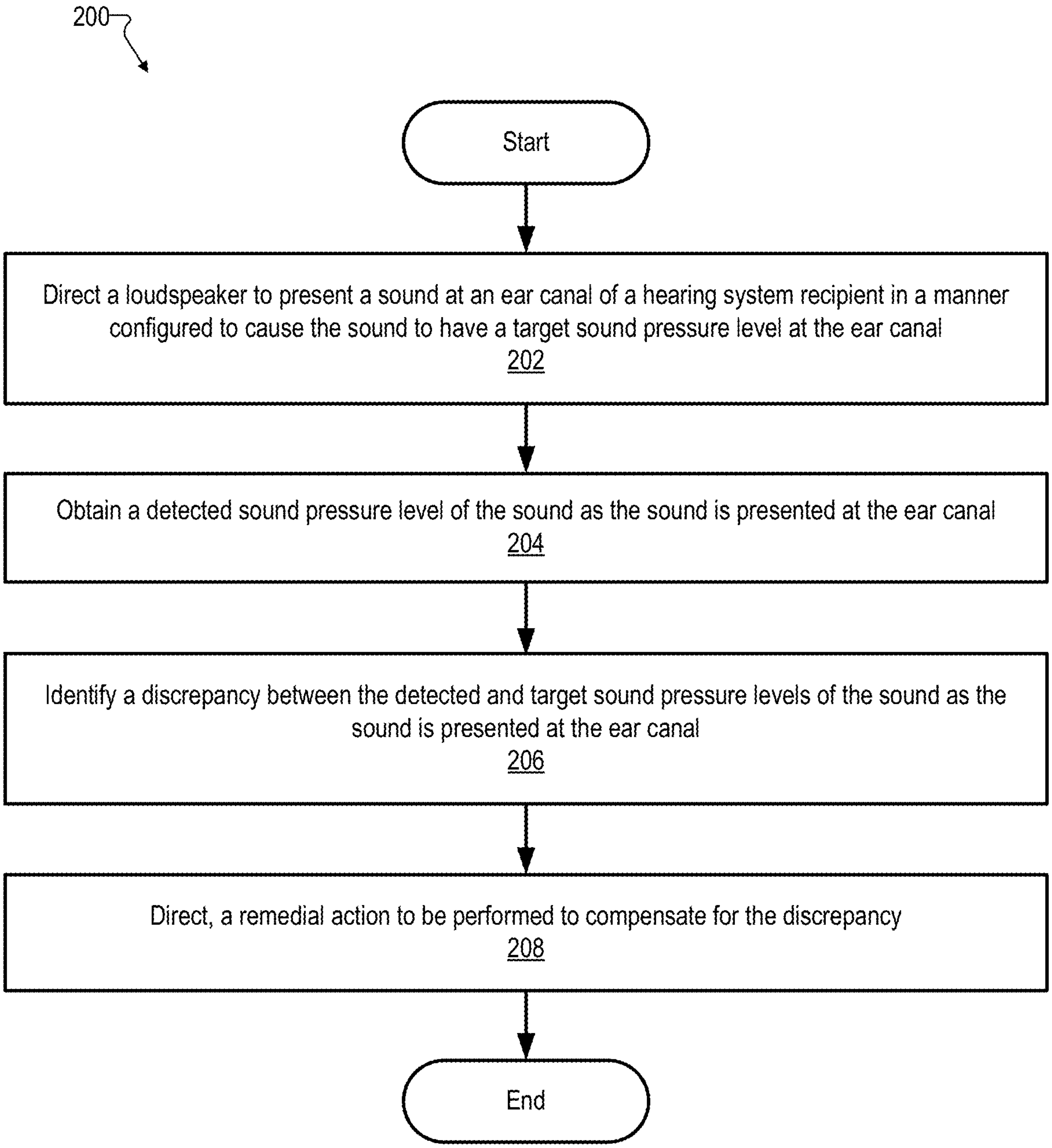
FIG. 2 shows an illustrative method for calibrating sound delivery to a hearing system recipient.

As one example of functionality that processor 104 may perform, FIG. 2 shows an illustrative method 200 for calibrating sound delivery to a hearing system recipient in accordance with principles described herein. While FIG. 2 shows illustrative operations according to one embodiment, other embodiments may omit, add to, reorder, and/or modify any of the operations shown in FIG. 2. In some examples, multiple operations shown in FIG. 2 or described in relation to FIG. 2 may be performed concurrently (e.g., in parallel)

with one another, rather than being performed sequentially as illustrated and/or described. One or more of the operations shown in FIG. 2 may be performed by a sound calibration system such as system 100 and/or any implementation thereof. For instance, method 200 may be performed by a system configuration device or electroacoustic hearing system described herein, or by other suitable systems or devices as may serve a particular implementation.

In some examples, the operations of FIG. 2 may be performed in real time so as to provide, receive, process, and/or use data described herein immediately as the data is generated, updated, changed, exchanged, or otherwise becomes available. Moreover, certain operations described herein may involve real-time data, real-time representations, real-time conditions, and/or other real-time circumstances. As used herein, "real time" will be understood to relate to data processing and/or other actions that are performed immediately, as well as conditions and/or circumstances that are accounted for as they exist in the moment when the processing or other actions are performed. For example, a real-time operation may refer to an operation that is performed immediately and without undue delay, even if it is not possible for there to be absolutely zero delay. Similarly, real-time data, real-time representations, real-time conditions, and so forth, will be understood to refer to data, representations, and conditions that relate to a present moment in time or a moment in time when decisions are being made and operations are being performed (e.g., even if after a short delay), such that the data, representations, conditions, and so forth are temporally relevant to the decisions being made and/or the operations being performed.

Each of operations 202-208 of method 200 will now be described in more detail as the operations may be performed by system 100, an implementation thereof, or another suitable stimulation system.

At operation 202, system 100 may direct a loudspeaker to present a sound to a hearing system recipient. For example, the loudspeaker may be located at least somewhat apart from the recipient (e.g., a few inches away, several feet away, etc.) and the sound may be presented by way of a length of tubing extending from the loudspeaker to an ear tip disposed at an ear canal of the hearing system recipient. In this manner, the sound that actually arrives at the ear canal may be controlled in ways that may not be possible when the sound is delivered without the use of the tubing and/or the ear tip (e.g., by way of open air).

The directing of the loudspeaker at operation 202 may be configured to cause the sound to have a target sound pressure level at the ear canal. As used herein, the directing of a loudspeaker is performed in a manner "configured to cause" sound to have a target sound pressure when the directing is performed with an aim, or in an attempt, to cause a resultant sound pressure of the sound to be the target sound pressure. For example, as the sound to be delivered to the recipient is generated, system 100 may direct the loudspeaker in a manner configured to cause the sound to have the target sound pressure level by accounting for known and expected effects that may contribute to the diminution of the sound pressure level of the sound as the sound is carried from the loudspeaker to the ear canal by the tubing and ear tip. It may be expected that the sound may drop by a particular number of decibels (dB) or by a particular percentage, for instance, so the sound may be produced at a slightly higher level than the sound pressure level targeted for the ear canal. As one example, the target sound pressure level at the ear canal may be 110 dB, while anticipated effects such as leakage, loudspeaker tolerances, and/or other mechanical effects may be expected to diminish the sound pressure level by 5 dB during transit from the loudspeaker to the ear canal. In this situation, operation 202 may involve directing the loudspeaker to produce the sound at a sound pressure level of 115 dB (i.e., 110 dB+5 dB) to cause the sound to have the target sound pressure level of 110 dB at the ear canal in spite of the anticipated effects.

It will be understood that, even when operation 202 is performed in a manner configured to cause the sound to be presented at the ear canal with a target sound pressure level, unanticipated effects (e.g., effects that are difficult to predict, plan for, and/or detect in real time) may cause the sound pressure level that is actually present at the ear canal and experienced by the recipient to be something other than the target sound pressure level. As such, performing operation 202 in a manner configured to cause the sound to have the target sound pressure level will be understood to employ the phrase "configured to" in a broader or more flexible sense than usual (or than might be used elsewhere herein). Specifically, while a typical usage of the "configured to" phrase might be understood to require that a particular result is actually achieved, "configured to" in this particular sense may refer to a goal or target that a system is intended to or meant to achieve even if the system is not necessarily perfectly successful in achieving the goal or target. For example, as mentioned above, unanticipated effects that may make it difficult to actually achieve the target sound pressure level at all times may include inadvertent kinking of the tubing that is carrying the sound from the loudspeaker to the ear canal, blockages in the ear tip that rests in the ear canal to deliver the sound from the tubing, fluid discharge or other foreign agents that may be unexpectedly present at the ear canal (or present to an unexpected degree), malfunctions or operation outside of accounted-for tolerances by sound delivery system components (e.g., the loudspeaker, the tubing, the ear tip, etc.), and/or any other unanticipated effects as may arise in a particular situation. Accordingly, operations 204-208 may be performed in conjunction with operation 202 to help mitigate, correct, and/or otherwise compensate for a failure of the loudspeaker, as a result of unanticipated effects that affect the sound delivery in a specific configuration, to present the sound at the target sound pressure level.

At operation 204, system 100 may obtain a detected sound pressure level of the sound as the sound is presented at the ear canal. While, as described above, the sound is generated at operation 202 in a manner that aims to achieve the target sound pressure level at the ear canal, operation 204 is performed to determine how successful or unsuccessful this targeting of operation 202 actually turned out to be. For instance, referring back to the specific example set forth above, if the anticipated effects actually only diminish the sound pressure level by 4 dB (instead of the 5 dB that is being accounted for) and unanticipated effects further diminish the sound pressure level by an additional 3 dB, the detected sound pressure obtained at operation 204 may be 108 dB (i.e., 115 dB generated −4 dB anticipated diminution −3 dB unanticipated diminution).

The actual sound pressure level of the sound at the ear canal may be detected and obtained by system 100 in any suitable way. For example, the detected sound pressure level may be detected and obtained from a probe microphone disposed within the ear tip. As will be described in more detail below, for instance, a probe microphone may include a microphone that is somewhat apart from the ear canal of the recipient and acoustically coupled to the ear tip at the ear canal by way of a length of tubing separate from the tubing coupling the loudspeaker to the ear tip. Sound present at the ear canal may be carried by this probe microphone tubing to be detected by the microphone and the microphone may provide data representative of a sound pressure level detected in this way to system 100, as will be described in more detail below.

In some examples, system 100 may continuously monitor the sound pressure level of the sound by way of the probe microphone as the sound is presented at the ear canal. In such examples, the obtaining of the detected sound pressure level at operation 204 may be performed as part of the continuous monitoring of the sound pressure level at the ear canal (rather than, for instance, as a one-time detection).

At operation 206, system 100 may identify a discrepancy between the detected sound pressure level obtained at operation 204 and the target sound pressure level of the sound as directed at operation 202. For instance, to use the example provided above in which the target sound pressure level was given as 110 dB and the detected sound pressure level was 108 dB, system 100 may identify a discrepancy of 2 dB (i.e., 110 dB−108 dB) between the detected and target sound pressure levels. In some examples, the identifying of the discrepancy may involve quantifying the difference in this way, while, in other examples, the identifying of the discrepancy may only including determining that there is a difference between the detected and target sound pressure levels (e.g., or that there is greater than a predetermined threshold difference between the levels) but not necessarily quantifying precisely what that difference is.

At operation 208, system 100 may direct, based on the discrepancy identified at operation 206, a remedial action to be performed to compensate for the discrepancy. As one illustrative remedial action, for instance, the generated sound pressure level produced by the loudspeaker may be adjusted so as to be more likely to achieve the target sound pressure level at the ear canal. Referring to the numerical example that has been provided in which a discrepancy of 2 dB has been identified, for example, system 100 may perform a remedial action of increasing the generated sound pressure level (15 dB) by the identified discrepancy (2 dB) to generate a sound pressure level of 17 dB (15 dB+2 dB) that is better configured to account for the 7 dB of diminution that has been detected and to thus achieve the 110 dB target sound pressure level.

In certain examples, it may not necessarily be possible or desirable to adjust the generated sound pressure level enough to compensate for a discrepancy that has been detected. For instance, the loudspeaker may already be providing a maximum sound pressure level that it is designed to provide and that sound pressure level may still fall short. As another example, it may be determined to present an unacceptable risk to increase the sound pressure level beyond a certain threshold since the recipient could experience discomfort or additional hearing damage if circumstances were to suddenly change as the high sound pressure level was being presented (e.g., if the tubing were suddenly unkinked, etc.). Accordingly, in these types of examples, other types of remedial actions other than adjusting the generated sound pressure level may be employed (e.g., in combination with or instead of the sound pressure level adjustments). For example, as will be described in more detail below, if the sound is presented for the purpose of evoking an auditory potential in the recipient for an audiometric test, test results may be modified or annotated to account for the discrepancy between the sound pressure level that was targeted for the test and the sound pressure level that was actually experienced by the recipient during the test.

Figure 3:
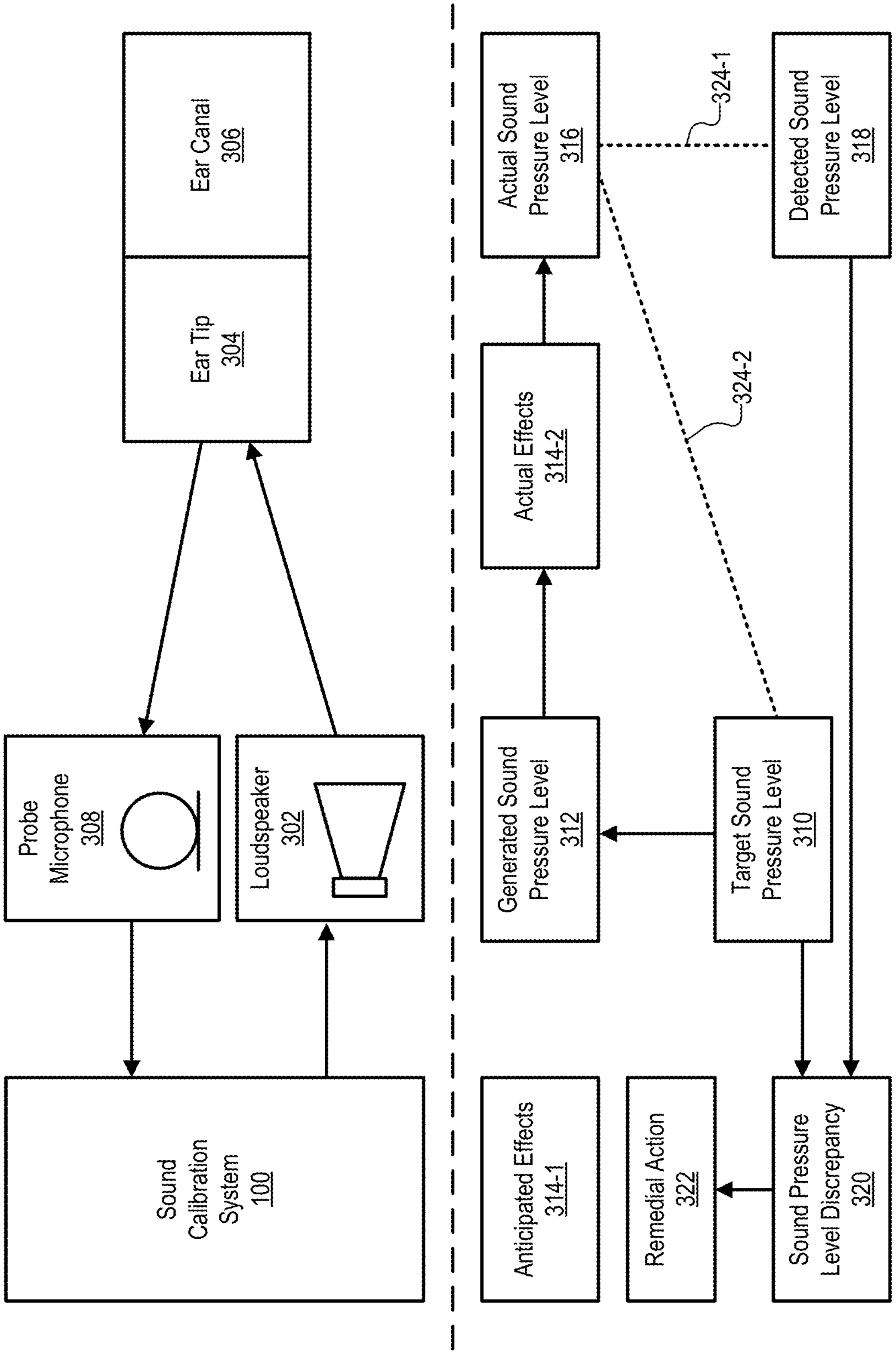
FIG. 3 shows various illustrative aspects of the sound calibration system of FIG. 1 as the system calibrates sound delivery to a hearing system recipient.

FIG. 3 shows various illustrative aspects of system 100 as system 100 calibrates sound delivery to a hearing system recipient in accordance with principles described herein. Specifically, certain physical aspects of the sound delivery are shown above a horizontal dashed line in FIG. 3. The physical aspects of the sound delivery shown in FIG. 3 include an implementation of system 100 that is coupled to a loudspeaker 302 configured to present a sound by way of an ear tip 304 at an ear canal 306 of a hearing system recipient. Also included is a probe microphone 308 configured to detect sound at ear canal 306 by way of ear tip 304, and to provide detected sound pressure levels back to system 100.

Below the dashed line in FIG. 3, various non-physical aspects of the sound delivery are also represented. Each of these aspects is placed beneath respective physical components to which the aspects correspond. Specifically, for example, FIG. 3 shows a target sound pressure level 310 that is used to set a generated sound pressure level 312 produced by loudspeaker 302 under direction of system 100, mechanical and/or other effects 314 (i.e., anticipated effects 314-1 that are predicted and planned for by system 100 and actual effects 314-2 that actually diminish the sound pressure level as the sound propagates from loudspeaker 302 to ear canal 306), an actual sound pressure level 316 at ear canal 306, a detected sound pressure level 318 at ear canal 306, a sound pressure level discrepancy 320 identified by system 100, and a remedial action 322 performed by or under direction of system 100. Each of the physical and non-physical aspects illustrated in FIG. 3 will now be described in more detail with reference to FIGS. 3, 4, 5A, and 5B.

Loudspeaker 302 may be implemented as a speaker of a device used for configuring or setting up a hearing system (e.g., a speaker of a lead insertion monitoring device used to capture acoustically-evoked responses during a lead insertion surgical procedure, a speaker of a clinician fitting device used to capture acoustically-evoked responses during a hearing system fitting session, etc.) or as an acoustic receiver of a hearing system itself (e.g., an acoustic receiver of as electroacoustic hearing system, a hearing aid system, etc.). In any of these implementations, loudspeaker 302 may be acoustically coupled to ear tip 304 by way of a length of tubing as ear tip 304 is disposed at ear canal 306 of the recipient to whom the sound is being presented. Probe microphone 308 may also be coupled to ear canal 306 by way of ear tip 304 and tubing that is part of the probe microphone design. These physical aspects of the sound delivery system are illustrated and described in more detail with reference to FIG. 4.

Figure 4:
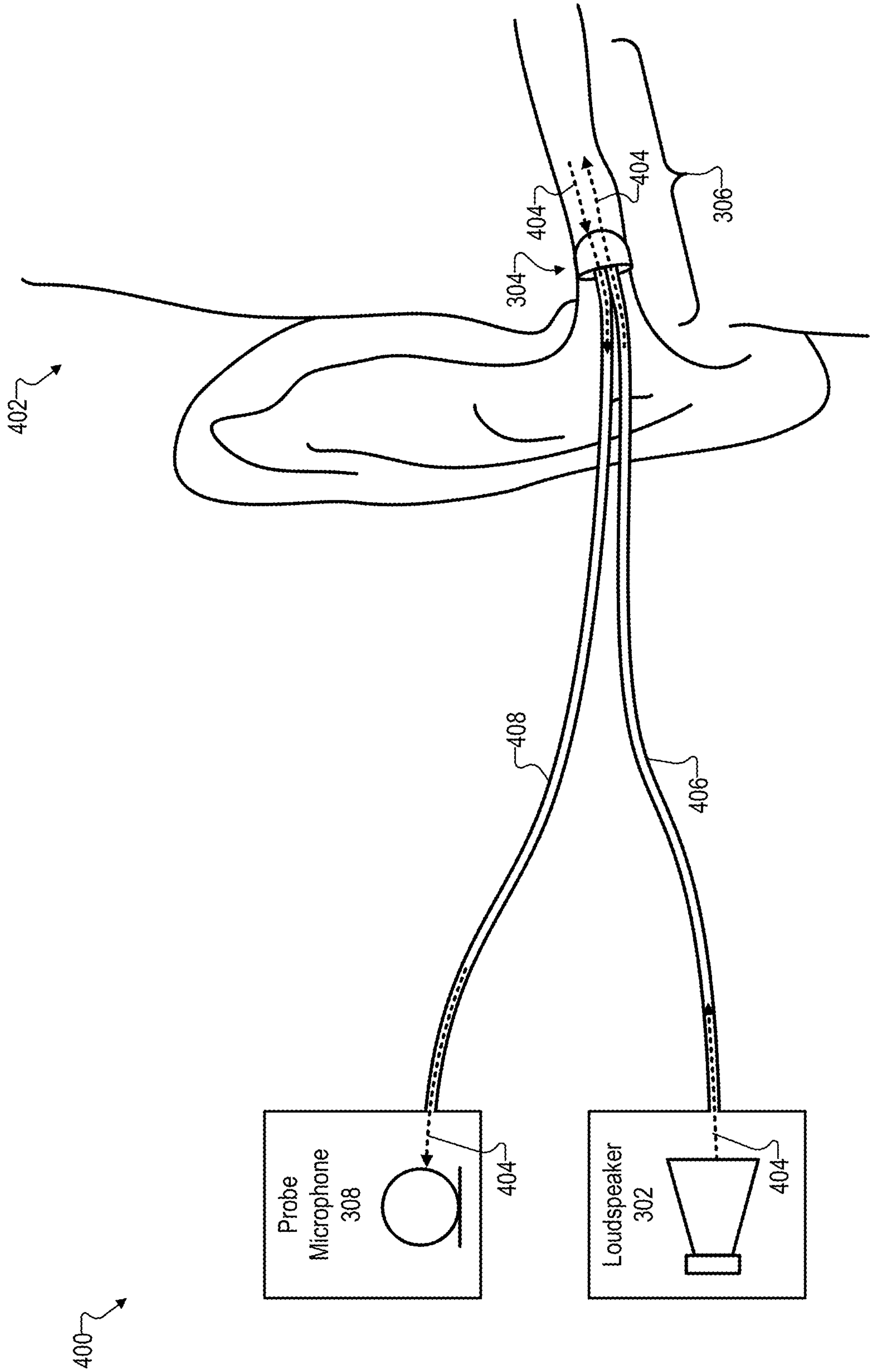
FIG. 4 shows an illustrative configuration in which calibrated sound is delivered to an ear canal of a hearing system recipient.

FIG. 4 shows an illustrative configuration 400 in which calibrated sound is delivered to ear canal 306 of a hearing system recipient 402. As shown in FIG. 4, loudspeaker 302 may generate a sound 404 that propagates through a length of tubing 406 that extends from loudspeaker 302 to ear tip 304 as ear tip 304 is worn by recipient 402 at ear canal 306. Sound 404 is shown to arrive at ear canal 306 to be heard by recipient 402, as well as to then propagate from ear canal 306 back through ear tip 304 to probe microphone 308 by way of an additional length of tubing 408.

While no unanticipated effects (e.g., kinking of tubing 406 as the tubing is taped down in preparation for a surgical procedure, fluid blockages of sound 404 caused by fluids associated with a surgical procedure, etc.) are explicitly shown in FIG. 4, it will be understood that such effects may be present to impede, diminish, or otherwise affect the propagation of sound 404 in certain situations. For instance, when a surgical operation such as a lead insertion procedure associated with implantation of a cochlear implant is ongoing, an incision may be present to allow the surgeon to insert an electrode lead into a cochlea of the recipient (not explicitly shown). During this procedure, a pinna of the ear of recipient 402 may be taped down so as to cover ear canal 306 (e.g., to help prevent fluids associated with the operation from reaching ear canal 306). Even if this taping is performed with great care, it can be difficult to ensure that no kinking of tubing 406 and/or 408 is present, to ensure that no amount of fluid has reached the ear canal to partially block sound 404, and so forth. Moreover, once the taping is done and surgery has commenced, it may be highly inconvenient and undesirable to make adjustments with respect to the tubing or to ear tip 304 even if issues are known to have arisen. Accordingly, as described herein, system 100 may calibrate sound delivery to recipient 402 prior to the commencement of the surgical procedure and during the surgical procedure so that issues can be manually or automatically addressed at convenient times and in convenient ways and will not interfere with the surgery.

Figure 5A:
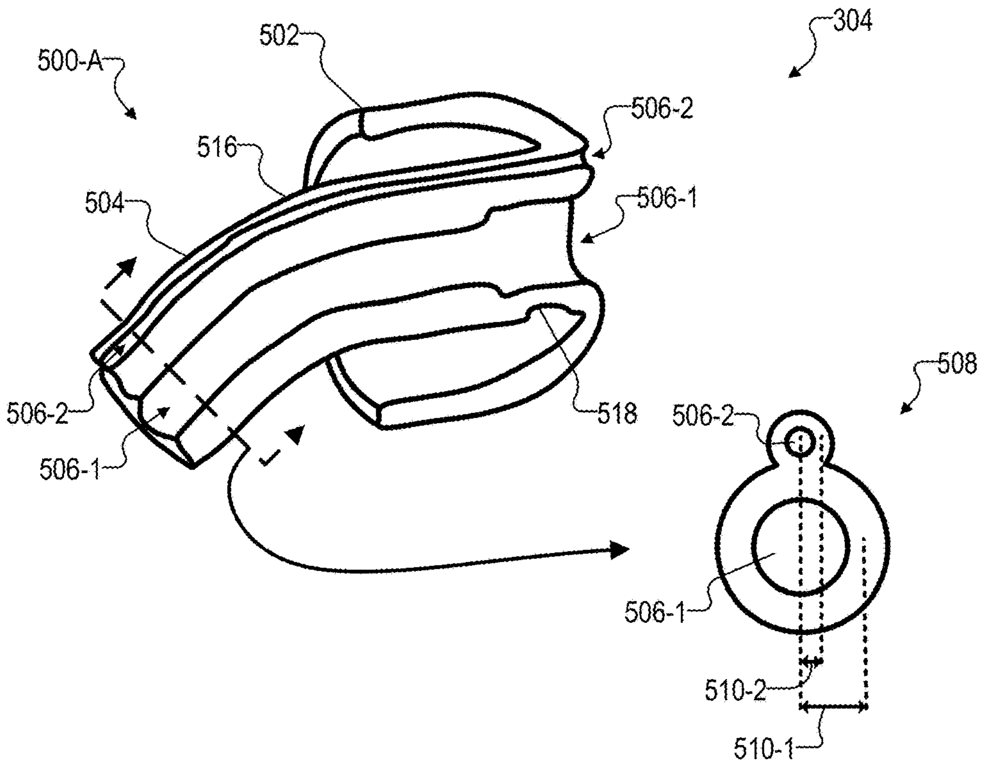
FIGS. 5A-5B show illustrative implementations for an ear tip used to deliver calibrated sound to a hearing system recipient.
Figure 5B:
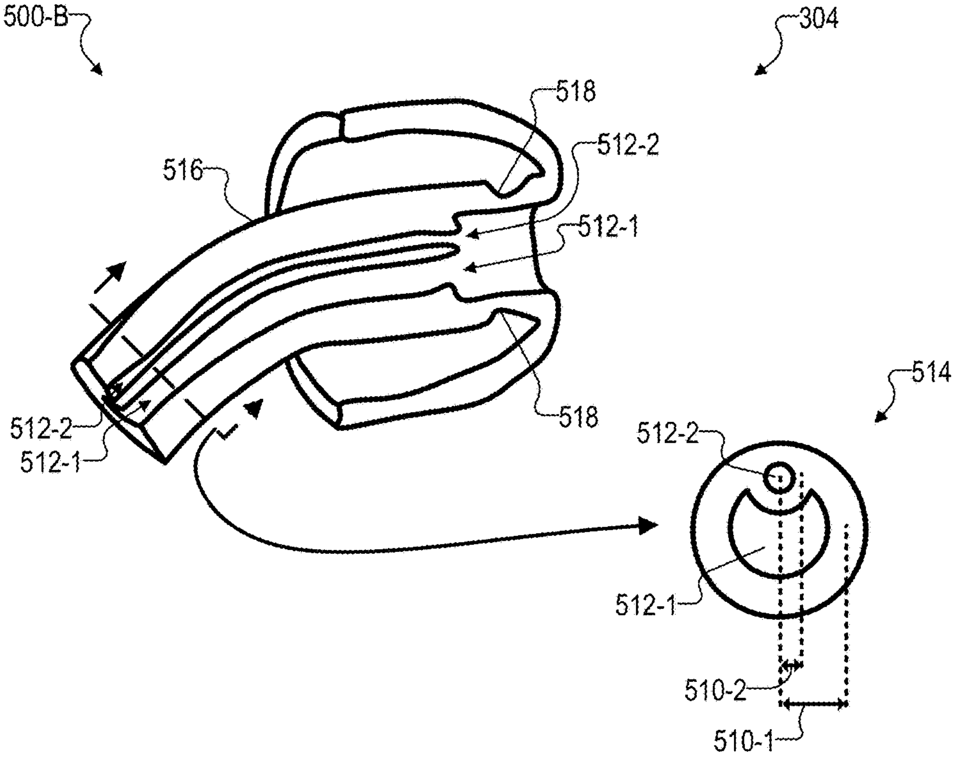

Ear tip 304 may include any of several potential features configured to facilitate ear tip 304 in playing its role in an effective and efficient delivery of calibrated sound to ear canal 306. To illustrate, FIGS. 5A-5B show example implementations 500 of ear tip 304 used to deliver calibrated sound to recipient 402. Specifically, an implementation 500-A (also referred to as ear tip 500-A) of ear tip 304 is shown in FIG. 5A, while an implementation 500-B (also referred to as ear tip 500-B) of ear tip 304 is shown in FIG. 5B.

Referring first to ear tip 500-A, FIG. 5A illustrates an exemplary cross section view of ear tip 500-A that is perpendicular to a longitudinal axis of the ear tip. As shown, ear tip 500-A includes an outer portion 502 that is configured to contact ear canal 306 and hold the ear tip in place, as well as an inner portion 504 that carries sounds such as sound 404 from tubing 406 into ear canal 306 and from ear canal 306 into tubing 408. In certain examples, separate and distinct channels may be included within an implementation of ear tip 304 so as to allow the ear tip to effectively carry sound to and from ear canal 306 during operation. For example, as illustrated by implementation 500-A, two separate and distinct channels 506 (i.e., channels 506-1 and 506-2) through inner portion 504 may be used to simultaneously carry sound toward and away from ear canal 306. Specifically, tubing 406 may carry sound 404 to recipient 402 by way of channel 506-1 of ear tip 500-A (e.g., by tubing 406 connecting to channel 506-1 at the proximal end of inner portion 504), while probe microphone 308 may detect the sound pressure level of sound 404 by way of channel 506-2 of ear tip 500-A (e.g., by tubing 408 connecting to channel 506-2 at the proximal end of inner portion 504). As shown in FIG. 5A, these channels 506-1 and 506-2 are physically separate channels within ear tip 500-A to allow sound waves to travel largely or entirely in a single direction within each channel (e.g., to the right towards ear canal 306 for channel 506-1, and to the left away from ear canal 306 for channel 506-2).

Channels 506 may be implemented within implementations of ear tip 304 in any suitable way. For instance, as shown by a lateral cross section 508 of internal portion 504 of ear tip 500-A, channel 506-1 may have an approximately circular cross section having a radius 510-1, channel 506-2 may have an approximately circular cross section having a radius 510-2 that is less than radius 506-1, and channel 506-2 may be disposed outside of channel 506-1 such that the cross section of channel 506-2 is immediately adjacent to the cross section of channel 506-1.

In contrast, FIG. 5B shows another way that channels 506 may be implemented within an implementation of ear tip 304. Specifically, as shown in FIG. 5B, ear tip 500-B may include many of the same features as ear tip 500-1 (e.g., an external portion, an internal portion, two channels, etc.), but channels 512 extending through the internal portion of ear tip 500-B (i.e., channels 512-1 and 512-2) are shown in a lateral cross section 514 to be configured differently from channels 506 described above. As with channels 506, channel 512-1 may have an approximately circular cross section having radius 510-1 and channel 512-2 may have an approximately circular cross section having smaller radius 510-2. However, in contrast to channels 506 in cross section 508, cross section 514 shows that channel 512-2 may be disposed within channel 512-1 such that the cross section of channel 512-2 is contained within the cross section of channel 512-1.

Besides the separate channels 506 and 512 shown to be integrated within ear tip implementations 500 in FIGS. 5A and 5B, additional features that may increase the effectiveness of the ear tips are also shown. For example, as shown, a permanent bend 516 may be built into the internal portion of each ear tip to help angle tubing connected to the ear tip toward a pinna of the recipient's ear so as to help reduce an interaction of a surgeon or other user with the tubing (e.g., tubing 406 and/or 408 connected to ear tip 304). As shown in the examples of both ear tips 500-A and 500-B, permanent bends 516 would help move tubing connected to the proximal end of the ear tip down and out of the way (e.g., in any direction as a surgeon may desire) so that the tubing does not stick straight out of ear canal 306 as may be the case with a conventional sound delivery apparatus. At the same time, permanent bends 516 may allow channels 506 and 512 to remain unobstructed by preventing kinking.

Another feature of ear tips 500-A and 500-B that may help these ear tips effectively play their role in calibrating sound delivery to a recipient is that the external portions of the ear tips (e.g., external portion 502 of ear tip 500-A) may be configured to interface with ear canal 306 of recipient 402 so as to acoustically isolate the interior of ear canal 306 from the exterior of the ear canal. For example, implementations 500 of ear tip 304 may be flexible to form a close fit within ear canal 306 such that channels 506 and/or 512 are the only air channels by way of which sound may propagate between the interior and exterior of ear canal 306. This close fit may make ear tip comfortable, ergonomic, and easy to position, and may allow for precise control of the sound pressure level in the ways described herein. In contrast, certain conventional ear tips designed for applications in which some leakage is tolerated or desirable rather than complete isolation (e.g., certain ear tips used for ear phones, ear plugs, etc.) may be intentionally designed to allow at least some leakage (e.g., some form of sound propagation channel other than sound propagation channels 506 and 512) by way of which ambient sound may reach the interior of ear canal 306.

Another feature of ear tips 500-A and 500-B that may help these ear tips effectively play their role in calibrating sound delivery to a recipient is that the internal portions of the ear tips (e.g., internal portion 504 of ear tip 500-A) may be connected to the external portions of the ear tips (e.g., external portion 502 of ear tip 500-A) by way of a narrowed neck 518. Neck 518 may be configured to allow the internal portion of an ear tip to flex with respect to the external portion while minimizing strain on the external portion. In this way, even if tubing or ear tips are inadvertently bumped during a system configuration session (e.g., during a surgical procedure after everything is taped down), the ear tip may be less likely to be dislodged so as to break the isolation seal and/or to otherwise adversely affect the controlled transmittal of sound to the ear canal at a target sound pressure level.

Yet another feature of ear tips 500-A and 500-B is that the ear tips may be constructed from biocompatible and sterilizable materials so as to be suitable for use within a sterile field associated with a surgical operation. For example, to provide a high degree of isolation and stability (e.g., so as to not become dislodged), certain conventional intraoperative sound delivery apparatuses have used a compressible/decompressible foam material designed to be inserted into the ear canal in a compressed state and to then decompress within the ear canal to form a strong seal with a good degree of stability and isolation. However, due to a porous nature of such foam material, it may not be possible to achieve a suitable level of sterilization in such materials to be safely used near a sterile field of a surgery. For example, even if the ear canal is intended to remain outside of the sterile field associated with a surgical operation, a risk of fluids inadvertently leaking or other unexpected events may exist that could potentially cause the ear canal to come within the sterile field, thereby rendering any unsterilized materials (e.g., such as foam ear tips) potentially hazardous to the recipient. Accordingly, implementations 500 of ear tip 304 may be constructed of sterilizable (e.g., nonporous) materials that are flexible enough to provide a good isolation seal.

Returning to FIG. 3, generated sound pressure level 312 is illustrated below loudspeaker 302 to represent the sound pressure level at which sounds such as sound 404 are generated to try to achieve target sound pressure level 310 at ear canal 306. To this end, generated sound pressure level 312 may initially be determined (e.g., by system 100 prior to directing loudspeaker 302 to generate the sound at generated sound pressure level 312) based on target sound pressure level 310 (i.e., the desired level at which sound is to be presented at ear canal 306) and anticipated effects 314-1. For instance, as described above, if target sound pressure level 310 is 110 dB in one particular example and anticipated effects 312-1 (e.g., the length of tubing 406, known leakage parameters for tubing 406 and ear tip 304, etc.) are expected to reduce generated sound pressure level 312 by 5 dB in transit from loudspeaker 302 to ear canal 306, then generated sound pressure level 312 may be 115 dB.

Because it may not be possible to anticipate and preemptively account for all mechanical and/or other effects that may factor into how sound pressure level 312 may be altered by the time sound 404 is delivered to ear canal 306, actual effects 314-2 that actually alter sound pressure level 312 as sound 404 is in transit may be different from anticipated effects 314-1. For example, actual effects 314-2 may be greater or less than anticipated effects 314-1 due to undesirable and unanticipated effects (e.g., kinking of tubing 406, fluid blockage of ear tip 304, etc.), inaccurately anticipated effects (e.g., components performing at a different levels within a tolerance range than has been accounted for, etc.), and/or various other reasons. However, it may be difficult or impractical to directly predict and/or measure actual effects 314-2, particularly after a system configuration session such as a surgical procedure or fitting session has commenced. Accordingly, rather than trying to directly predict and/or measure the actual effects 314-2 that lead to the actual sound pressure level 316 presented at ear canal 306, system 100 may obtain (e.g., from probe microphone 308 under direction of system 100) detected sound pressure level 318.

Detected sound pressure level 318 is shown under ear canal 306 in FIG. 3 together with actual sound pressure level 316 since both of these represent the sound pressure level presented at ear canal 306 and should therefore be the same value or very close to one another. It will be understood that detected sound pressure level 318 may not perfectly reflect actual sound pressure level 316 under all circumstances because probe microphone 308 and its tubing 408 may also have tolerances and be subject to mechanical and/or other effects that must be accounted for. However, it has been found that a relationship 324-1 between actual sound pressure level 316 and detected sound pressure level 318 (represented by a dotted line in FIG. 3) is more predictable and stable than a relationship 324-2 between actual sound pressure level 316 and target sound pressure level 310 (represented by another dotted line in FIG. 3). As such, optimal results, albeit not necessarily perfect results, may be achieved when system 100 presumes that detected sound pressure level 318 (or a version of detected sound pressure level 318 that accounts for known effects) is equal to actual sound pressure level 316.

Based on target sound pressure level 310 and detected sound pressure level 318, system 100 may identify sound pressure level discrepancy 320. For example, if target sound pressure level 310 and detected sound pressure level 318 are different to at least a threshold degree (e.g., greater than 1 dB, greater than 3 dB, etc.) system 100 may determine that remedial action 322 is to be performed to compensate for discrepancy 320. In certain examples, the identification of discrepancy 320 may include calculating a value of the discrepancy between target sound pressure level 310 and detected sound pressure level 318 so that the identified value can be used to optimize remedial action 322.

Remedial action 322 may be performed by system 100 to compensate for (e.g., correct, mitigate, resolve, or otherwise address) discrepancy 320 between target sound pressure level 310 (i.e., the sound pressure level desired to be presented at ear canal 306) and detected sound pressure level 318 (i.e., the sound pressure level most likely to be actually presented at ear canal 306) in any manner as may serve a particular implementation. As one example, system 100 may direct remedial action 322 by directing a user (e.g., a clinician responsible for care of the recipient with respect to the hearing system, the recipient himself or herself, a caretaker of the recipient such as a parent or guardian of the recipient, etc.) to resolve an unanticipated effect associated with loudspeaker 302, the length of tubing 406, or ear tip 304. For example, system 100 may direct the user to search for kinks in tubing 406, to ensure that a proper isolation seal is produced by the seating of ear tip 304 in ear canal 306, to verify that no fluid or other foreign agents have gotten into ear canal 306 to block the sound, to manually check that loudspeaker 302 is producing sound 404 at the generated sound pressure level 312 that has been set, and so forth.

As another example, system 100 may direct remedial action 322 by directing loudspeaker 302 to adjust the sound pressure level at which sound 404 is presented to recipient 402 (i.e., generated sound pressure level 312) in a manner that decreases discrepancy 320 between detected and target sound pressure levels 318 and 310. For example, if discrepancy 320 indicates that detected sound pressure level 318 is higher than target sound pressure level 310, system 100 may direct loudspeaker 302 to adjust generated sound pressure level 312 downward in a stepwise fashion (e.g., until the discrepancy disappears) or by a determined value for discrepancy 320 (e.g., by 5 dB if the value of discrepancy 320 is 5 dB). Conversely, if discrepancy 320 indicates that detected sound pressure level 318 is lower than target sound pressure level 310, system 100 may direct loudspeaker 302 to adjust generated sound pressure level 312 upward in a stepwise fashion (e.g., until the discrepancy disappears) or by a determined value for discrepancy 320 (e.g., by 5 dB if the value of discrepancy 320 is 5 dB).

In certain examples that will be described in more detail below, recipient 402 may be a recipient of a hearing system that is set up for the recipient during a system configuration session such as a surgical insertion procedure (e.g., to implant an electrode lead into the cochlea of a cochlear implant system recipient) or a hearing system fitting session (e.g., a clinical session to properly customize stimulation parameters of a cochlear implant system or other hearing system to be tailored to the recipient). In such sessions, loudspeaker 302 may be included within a system configuration device configured to perform audiometric tests such as by evoking and measuring electrocochleographic ("ECochG") potentials, auditory brainstem responses ("ABRs"), or other such evoked responses produced by recipient 402 during the system configuration session. In these examples, system 100 may direct remedial action 322 by directing the system configuration device to account for the discrepancy 320 between the detected and target sound pressure levels 318 and 310 in an analysis of the measured ECochG potentials. For instance, the ECochG potentials that are measured may be adjusted to reflect detected sound pressure level 318 (rather than target sound pressure level 310) or may be annotated with detected sound pressure level 318 or discrepancy 320 so as to be accurately and effectively interpreted by any person or system that may analyze the ECochG test results for any purpose.

In certain examples, more than one remedial action 322 may be directed by system 100. For instance, a serial or parallel combination of remedial actions 322 such as those described above may be directed to address issues from several different angles or approaches. In certain implementations, a predetermined series of progressive remedial actions 322 may be directed (e.g., suggested for manual performance, automatically performed, etc.) by system 100 until discrepancy 320 disappears (or falls below a predetermined threshold) or until the entire series of remedial actions 322 has been completed. For example, one series of remedial actions 322 may involve directing a user of system 100 to manually verify that the correct generated sound pressure level 312 is being output by loudspeaker 302; then directing the user to search for electrical, mechanical, and/or other obstructions of the sound; then directing the user to make physical adjustments to mechanical components (e.g., tubing 406, ear tip 304) and/or electrical components (e.g., loudspeaker 302) to the extent possible in light of component tolerances and recipient safety considerations; then automatically adjusting (e.g., in software) measured physiological responses and/or estimated physiological thresholds based on whatever discrepancy 320 has not yet been resolved.

Figure 6:
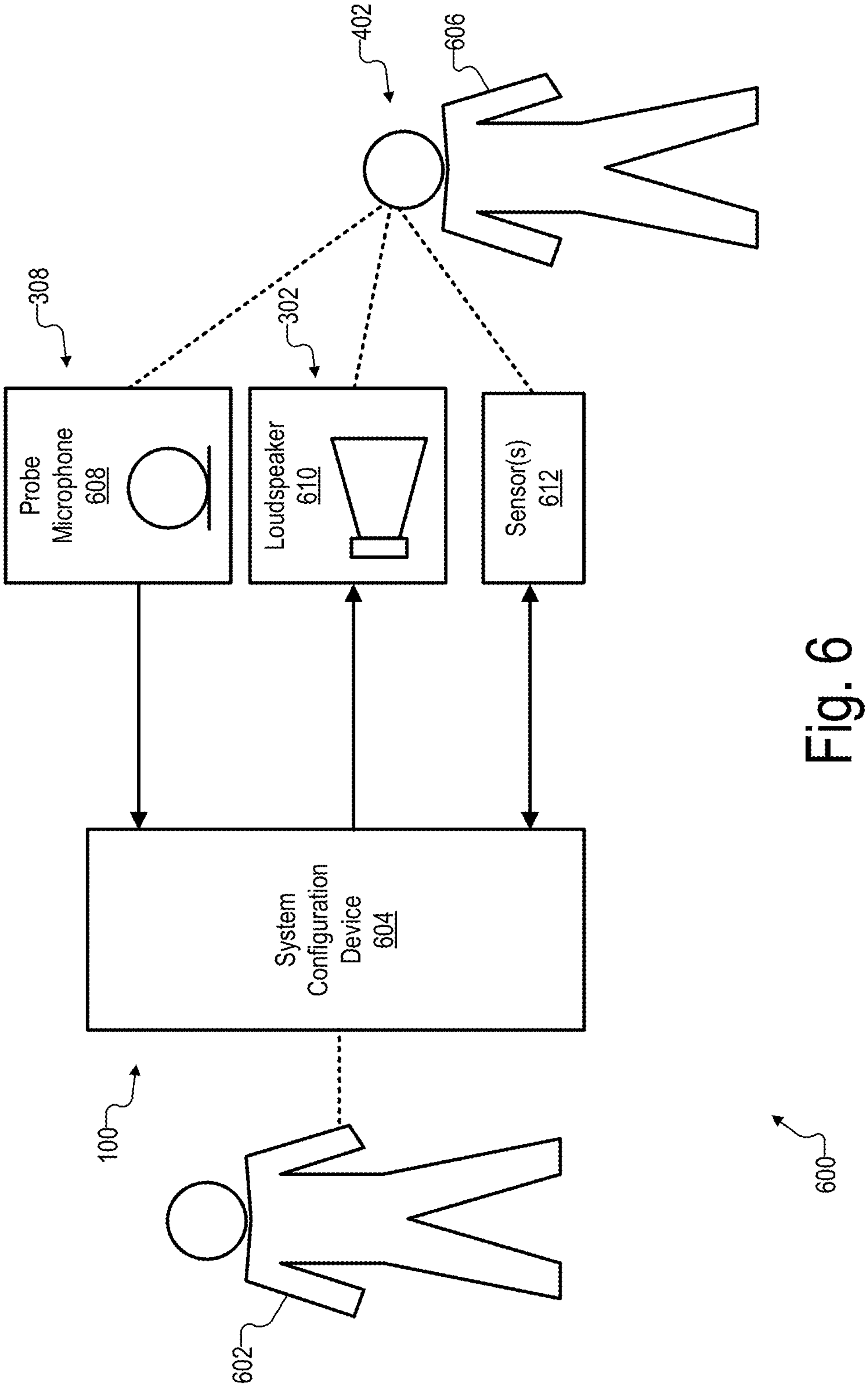
FIG. 6 shows an illustrative system configuration session during which a clinician uses an illustrative system configuration device to configure a hearing system with respect to a recipient.

FIG. 6 shows an illustrative system configuration session 600 during which a user 602 uses a system configuration device 604 to configure a hearing system with respect to a recipient 606. As shown, system configuration device 604 may be an implementation of system 100 and, as such, may be coupled with a probe microphone 608 (e.g., an implementation of probe microphone 308 described above) and with a loudspeaker 610 (e.g., an implementation of loudspeaker 302 described above). As has been described with respect to probe microphone 308, loudspeaker 302, and recipient 402, probe microphone 608 and loudspeaker 610 may be coupled to recipient 606 (who is analogous to recipient 402) by way of tubing and ear tips such as have been described.

Along with the probe microphone and loudspeaker coupled to the recipient, analogs of which have been described in detail above, FIG. 6 further shows one or more sensors 612 that are further coupled to recipient 606 and in communication with system configuration device 604 for purposes of system configuration session 600. Sensors 612 may represent any of various types of sensors that may be used to detect audiometric, physiological, neurological, and/or other evoked response, conditions, and/or characteristics of recipient 606. In some examples, sensors 612 may perform tests that involve acoustic stimulation (e.g., calibrated sound aimed at evoking involuntary responses from recipient 606, etc.). As such, sensors 612 may rely on an implementation of system 100 included within system configuration device 604, as well as probe microphone 608 and loudspeaker 610, to ensure that calibrated sound suitable for the testing is consistently delivered to the ear canal of recipient 606.

Sensors 612 may detect conditions and/or characteristics of recipient 606 using any suitable tests or techniques as may serve a particular implementation. For instance, sensors 612 may use or be implemented by an implanted cochlear or other ECochG electrode for detecting acoustically-evoked ECochG responses or ABRs from recipient 606, an electroencephalogram ("EEG") sensor for detecting a brain wave pattern of the recipient (e.g., an evoked or non-evoked potential, an auditory potential, a cortical potential, etc.), or another suitable sensor or tool as may serve a particular implementation.

Figure 7:
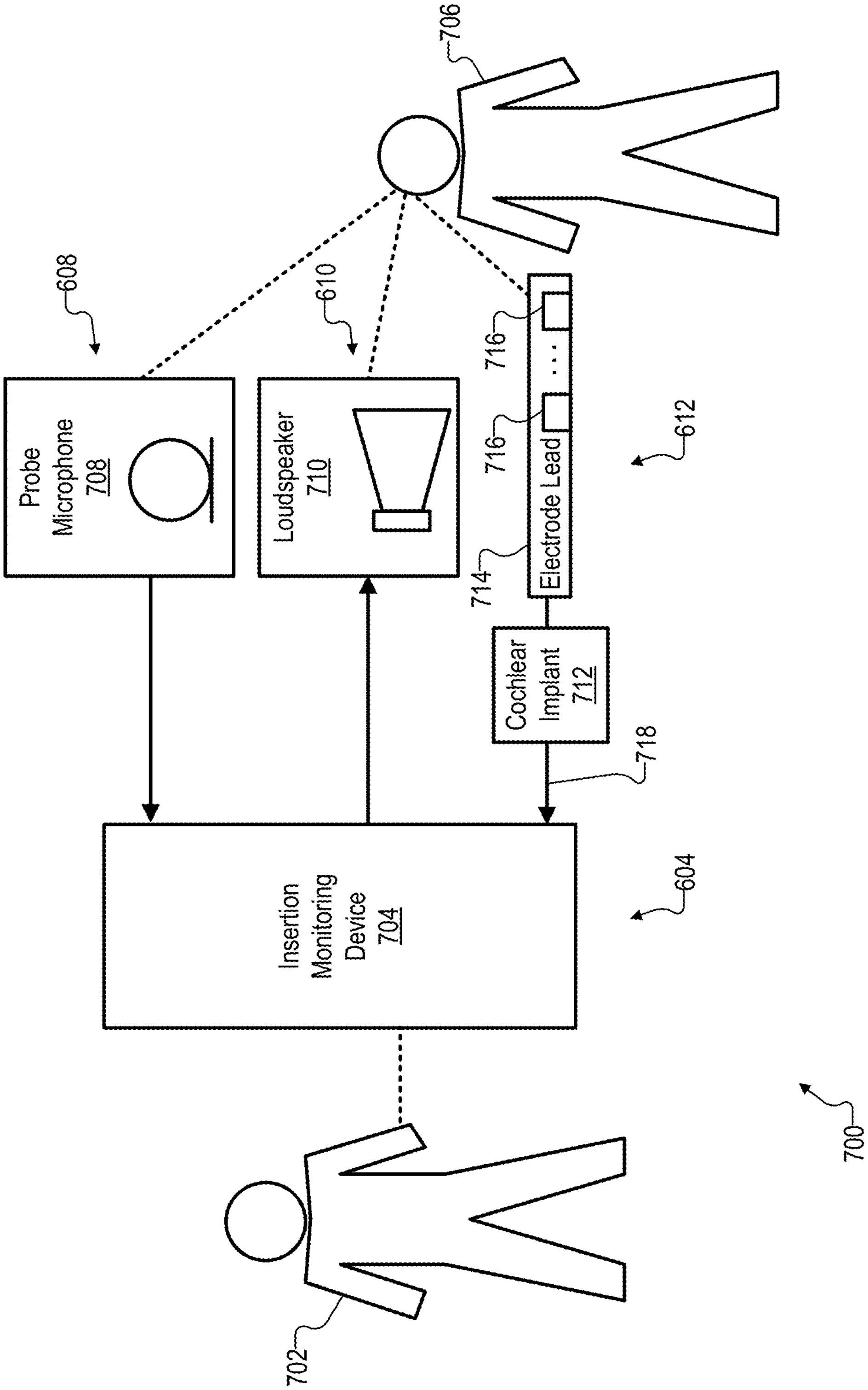
FIG. 7 shows an illustrative surgical insertion procedure implementing the system configuration session of FIG. 6.
Figure 8:
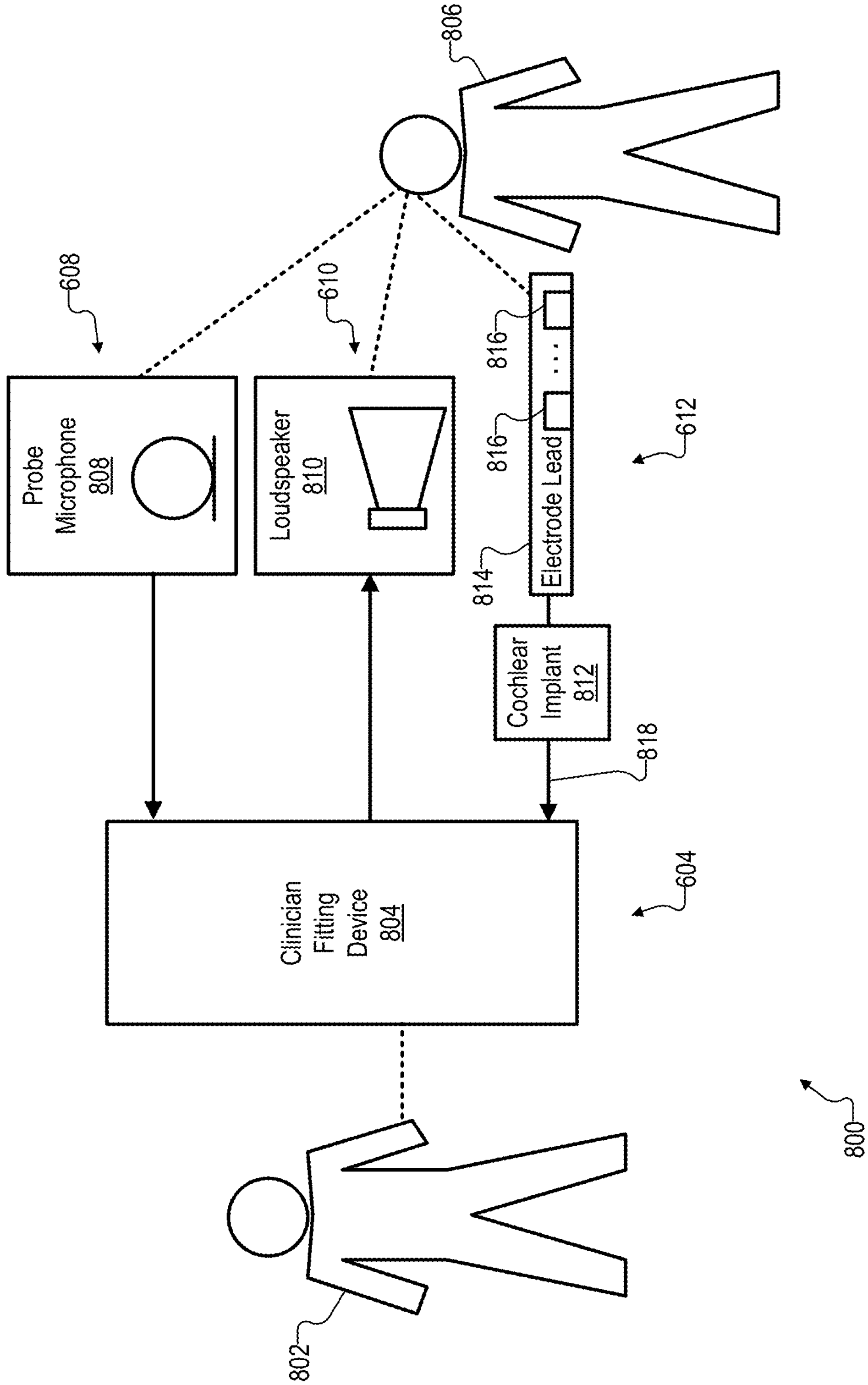
FIG. 8 shows an illustrative hearing system fitting session implementing the system configuration session of FIG. 6.
Figure 9:
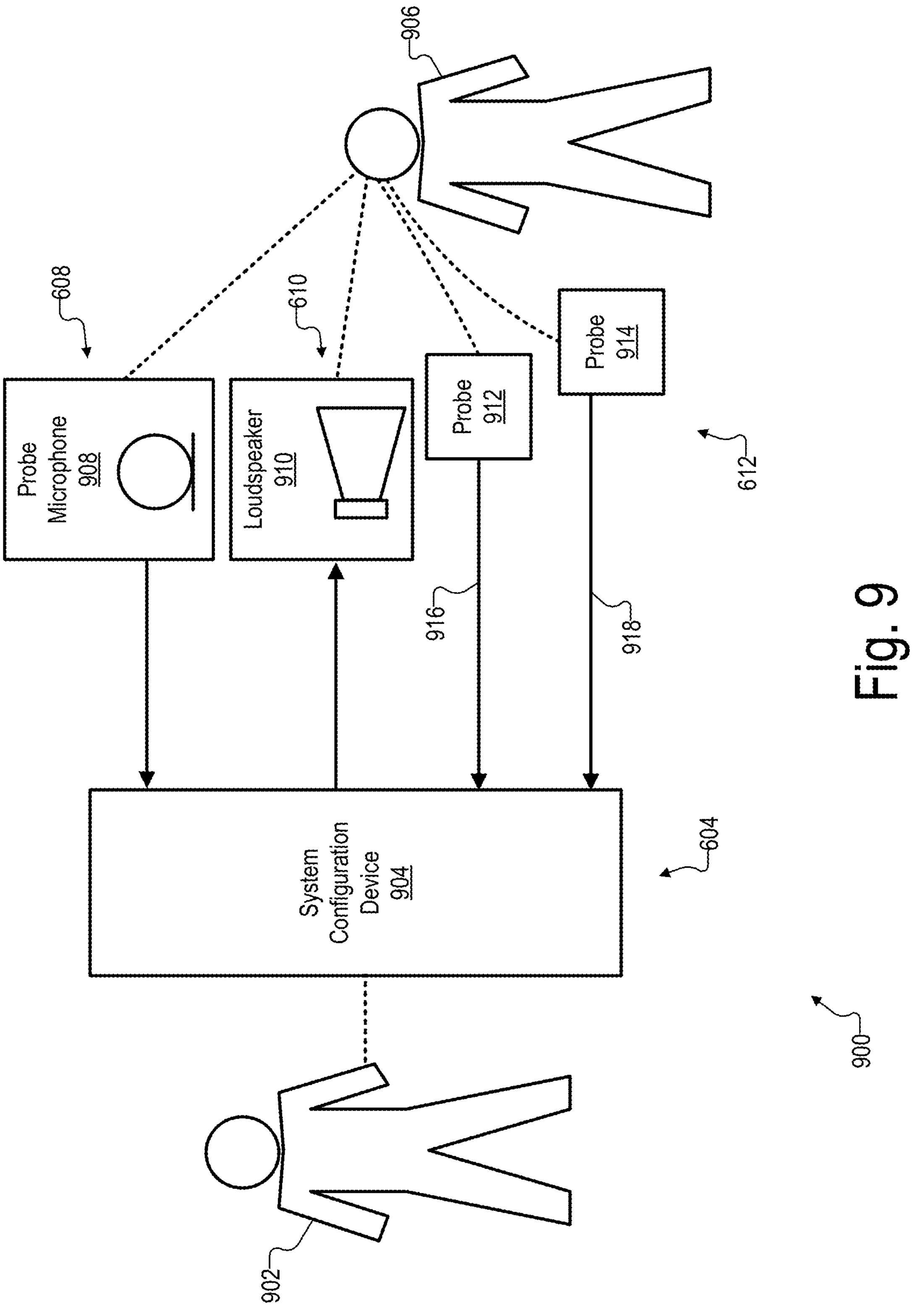
FIG. 9 shows an illustrative implementation of the system configuration session of FIG. 6 that involves a plurality of different sensors.

FIGS. 7-9 show different implementations of system configuration session 600. Specifically, FIG. 7 shows an illustrative surgical insertion procedure 700 implementing system configuration session 600, FIG. 8 shows an illustrative hearing system fitting session 800 implementing system configuration session 600, and FIG. 9 shows an illustrative implementation 900 of system configuration session 600 (also referred to as system configuration session 900) that involves a plurality of different sensors. In each of FIGS. 7-9, components analogous to system configuration device 604, probe microphone 608, loudspeaker 610, and sensors 612 are included and labeled with external reference designators pointing to the components. Unless otherwise noted, these analogous components will not be described in detail and will be understood to perform the same or similar functionality as analogous components that have already been described.

Surgical insertion procedure 700 of FIG. 7 includes a surgical team member 702 (e.g., a surgeon or another practitioner assisting in performing surgical insertion procedure 700) that uses an insertion monitoring device 704 analogous to system configuration device 604 (and therefore implementing system 100). Insertion monitoring device 704 may be specifically configured to monitor the condition of a recipient 706 who is receiving the surgery as the surgical procedure is performed. A probe microphone 708 and a loudspeaker 710 may be integrated within or coupled with insertion monitoring device 704 for use in monitoring the condition of recipient 706 during the surgery. For example, recipient 706 may be a recipient of a cochlear implant system that implements sensors 612 and includes a cochlear implant 712 and an electrode lead 714 having a plurality of electrodes 716. These components of the cochlear implant system may be implanted within recipient 706 during surgical insertion procedure 700 while other components of the cochlear implant system (e.g., a sound processor, a headpiece, and/or other cochlear implant system components that will be described in more detail below) may remain external to recipient 706 as the procedure is performed.

In the example of FIG. 7, loudspeaker 710 may be included within insertion monitoring device 704 and may be configured to evoke and measure ECochG potentials 718 produced by recipient 706 as surgical insertion procedure 700 is performed. For example, ECochG potentials 718 may be evoked in recipient 706 by sound delivered by loudspeaker 710 and calibrated to a target sound pressure level using probe microphone 708 (as has been described), may be measured by one or more electrodes 716 of electrode lead 714 under direction from cochlear implant 712, and may be reported back to system 100 (e.g., to insertion monitoring device 704) by cochlear implant 712. Additional examples and detail regarding cochlear implant systems will be provided below.

Fitting session 800 of FIG. 8 includes a clinician 802 who is tasked with using a clinician fitting device 804 analogous to system configuration device 604 (and therefore implementing system 100) to customize a cochlear implant system to a recipient 806. The cochlear implant system may be a standard cochlear implant system that only applies electrical stimulation or an electroacoustic hearing system that provides both electrical and acoustic stimulation. Clinician fitting device 804 may be specifically configured to monitor the condition of recipient 806 during the fitting session as different stimulation is provided to try to determine various customizable parameters for recipient 806 (e.g., a minimum sound pressure level that recipient 806 is capable of perceiving, a most comfortable sound pressure level for recipient 806, a maximum sound pressure level before recipient 806 finds sound to be uncomfortably or painfully loud, etc.).

A probe microphone 808 and a loudspeaker 810 may be integrated within or coupled with clinician fitting device 804 for use in monitoring the condition of recipient 806 during the fitting session. For example, as with recipient 706, recipient 806 may be a recipient of hearing system such as a cochlear implant system that implements sensors 612 and includes a cochlear implant 812 and an electrode lead 814 having a plurality of electrodes 816. Parameters configured to customize operation of these components to be optimal for recipient 806 may be determined during fitting session 800. In the example of FIG. 8, loudspeaker 810 may be included within clinician fitting device 804 and may be configured to evoke and measure ECochG potentials 818 produced by recipient 806 as fitting session 800 is performed. For example, ECochG potentials 818 may be evoked in recipient 806 by sound delivered by loudspeaker 810 and calibrated to a target sound pressure level using probe microphone 808 (as has been described), may be measured by one or more electrodes 816 of electrode lead 814 under direction from cochlear implant 812, and may be reported back to system 100 (e.g., to clinician fitting device 804) by cochlear implant 812.

Fitting sessions such as fitting session 800 that involve involuntary evoked responses such as ECochG potentials 818 may lead to desirable outcomes for recipients who may have difficulty in expressing or articulating their subjective experiences. For example, it may be useful to determine how a recipient's brain responds to different stimuli if the recipient is a small child who is unable to provide reliable behavioral feedback. Similarly, systems and methods described herein may provide significant fitting improvements for recipients with disabilities that affect speech or understanding (e.g., such that the recipients have difficulty in providing verbal or other behavioral feedback), as well as for recipients who suffer from auditory neuropathy.

System configuration session 900 of FIG. 9 may represent a surgical insertion procedure (e.g., similar to surgical insertion procedure 700 of FIG. 7), a fitting session (e.g., similar to fitting session 800 of FIG. 8), or another suitable session during which a hearing system is set up or configured with respect to a recipient in any manner as may serve a particular implementation. A user 902 representing a surgeon, a clinician, or another person overseeing system configuration session 900 is shown to use a system configuration device 904 (analogous to system configuration device 604, and therefore implementing system 100) to perform system configuration session 900 (e.g., to perform a lead insertion procedure, to customize a hearing system, etc.) with respect to a recipient 906.

A probe microphone 908 and a loudspeaker 910 may be integrated within or coupled with system configuration device 904 for use in monitoring the condition of recipient 906 during system configuration session 900 in connection with a plurality of different sensors implementing sensors 612. Specifically, in the example of FIG. 9, a first probe 912 and a second probe 914 are shown to implement sensors 612. Probes 912 and 914 may represent any types of sensors configured to detect real-time evoked responses or other physiological conditions or characteristics of recipient 906 in any way as may serve a particular implementation. For example, similar to the cochlear implant system implementations of sensors 612 in FIGS. 7 and 8, probe 912 may represent an electrode of a cochlear implant lead configured to detect one or more ECochG potentials 916. Specifically, loudspeaker 910 may be included within system configuration device 904 and may be configured to evoke and measure ECochG potentials 916 produced by recipient 906 during system configuration session 900. For example, ECochG potentials 916 may be evoked in recipient 906 by sound delivered by loudspeaker 910 and calibrated to a target sound pressure level using probe microphone 908 (as has been described), and may be measured by probe 912 under direction from system configuration device 904.

Probe 914 may represent another type of internal or external sensor used to perform an electroencephalogram (EEG) test or other suitable test distinct from testing performed by probe 912. For instance, probe 914 may be implemented as an electrode worn outside the head of recipient 906, as an implanted electrode that may or may not be associated with an electrode of a cochlear implant electrode lead, or as another suitable sensor. Probe 914 may be configured to detect evoked cortical potentials or other brain functions produced by recipient 906 in response to calibrated acoustic stimulation presented using loudspeaker 910, probe microphone 908, and an implementation of system 100 included within system configuration device 904. For example, along with obtaining ECochG potentials 916 from probe 912, system 100 may further obtain EEG test results 918 from an EEG test performed using probe 914 with respect to recipient 906 during system configuration session 900.

In some examples, system 100 may identify sound pressure level discrepancy 320 between detected sound pressure level 318 and target sound pressure level 310 based not only on sound pressure levels detected by probe microphone 308, but also based on EEG test results 918, ECochG potentials 916, and/or other sensor data. As mentioned above, unanticipated effects such as mechanical issues related to tubing kinks, sound blockages, and so forth, may potentially interfere with the sound pressure level monitoring performed by probe microphone 308 similarly as these issues may interfere with sound delivery by loudspeaker 302. While the issues may be less likely to manifest on the monitoring side, information obtained from sensors 612 such as probes 912 and/or 914 may help verify that data obtained from probe microphone 908 is accurate and can be trusted. In some examples, ECochG potentials 916 and/or EEG test results 918 obtained from these probes may indicate the actual sound pressure level 316 perceived by recipient 906, and may thus serve as a check on detected sound pressure level 318 obtained from the probe microphone.

While FIGS. 6-9 have illustrated how system 100 may be implemented with respect to different hearing system configuration sessions and setups, it will be understood that principles described herein may also be employed under circumstances other than relatively rare system configuration sessions like surgeries or clinical fitting sessions. For instance, in the case of an electroacoustic hearing system that provides acoustic stimulation to a recipient and includes electrodes capable of serving as sensors (e.g., for ECochG, EEG, ABR, and/or other types of monitoring), methods and techniques described herein may be performed as part of normal day-to-day operation of the electroacoustic hearing system.

Figure 10:
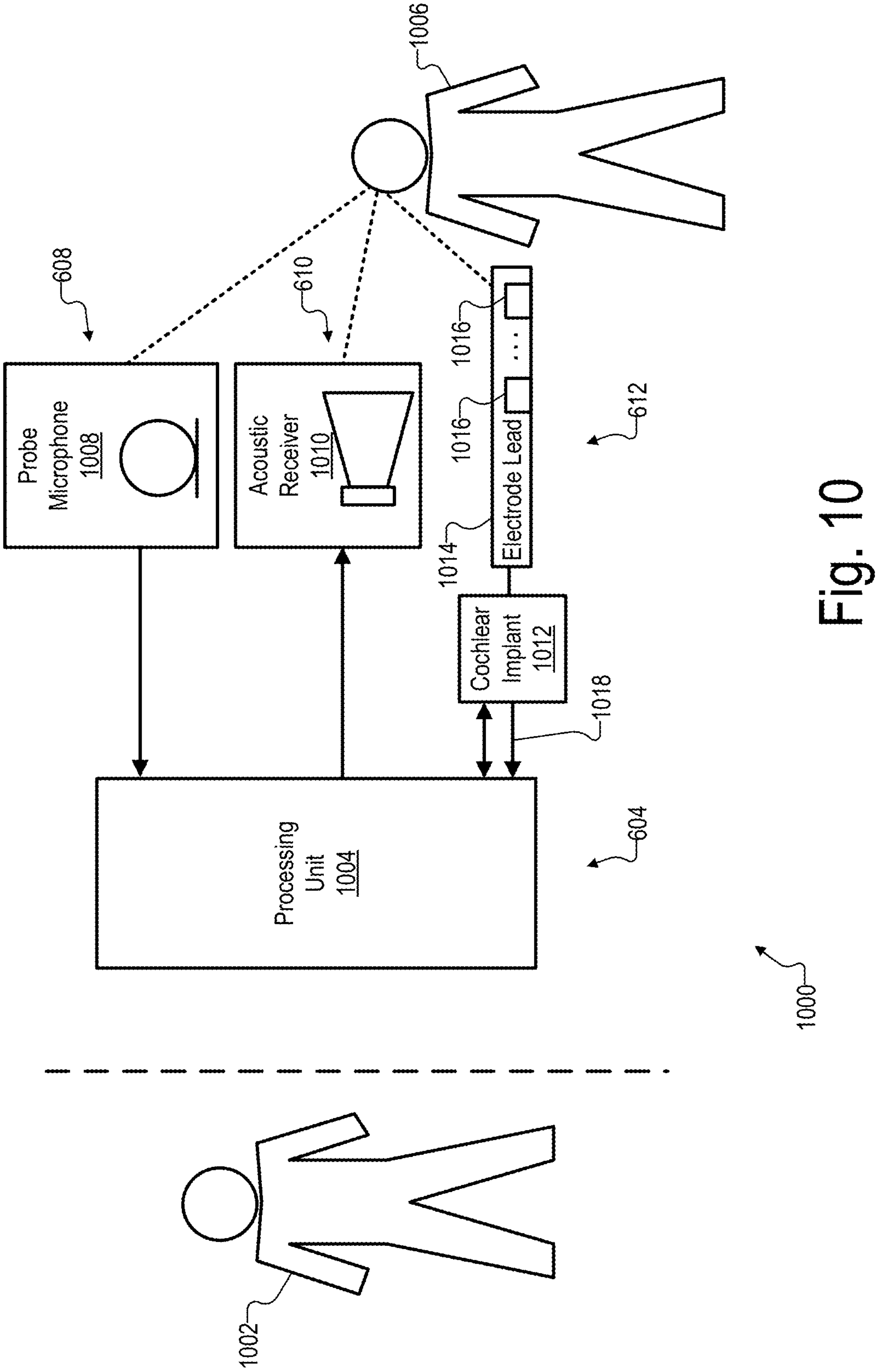
FIG. 10 shows an illustrative electroacoustic hearing system configured to calibrate sound delivery to a hearing system recipient during normal operation of the electroacoustic hearing system.

To illustrate, FIG. 10 shows an example electroacoustic hearing system 1000 that implements system 100 and, as such, is configured to calibrate sound delivery to a hearing system recipient during normal operation. As shown, a user 1002 such as a surgeon, clinician, caretaker, or other person involved with system configuration sessions described above, may be separate and not directly involved with electroacoustic hearing system 1000 during normal operation. This separation is indicated by a dashed line separating user 1002 from electroacoustic hearing system 1000 and a recipient 1006 who is outfitted with electroacoustic hearing system 1000.

Electroacoustic hearing system 1000 is shown to include a processing unit 1004 communicatively coupled with a probe microphone 1008 (analogous to probe microphone 608), an acoustic receiver 1010 (analogous to loudspeaker 610), and a cochlear implant 1012 coupled with an electrode lead 1014 having a plurality of electrodes 1016 (which, collectively, may apply electrical stimulation to recipient 1006 and may also serve as probes or sensors analogous to sensors 612). Acoustic receiver 1010 may be configured to apply acoustic stimulation to recipient 1006 during normal operation of electroacoustic hearing system 1000 while cochlear implant 1012 and electrode lead 1014 may be configured, when implanted within recipient 1006, to apply electrical stimulation to recipient 1006 during the normal operation of electroacoustic hearing system 1000. Acoustic receiver 1010 implements a loudspeaker configured to present calibrated sound to recipient 1006 during normal operation under direction of processing unit 1004 (e.g., a sound processor of the electroacoustic hearing system) and based on feedback from probe microphone 1008, evoked potentials 1018 (e.g., ECochG potentials, EEG potentials, etc.) detected by cochlear implant 1012 and electrode lead 1014, and/or other input to the system.

The components of electroacoustic hearing system 1000 may operate similarly or analogously with like components in other implementations of system 100 described herein. For example, acoustic receiver 1010 may be configured to apply acoustic stimulation to recipient 1006 by way of an ear tip disposed at an ear canal of recipient 1006 (not explicitly shown in FIG. 10). Probe microphone 1008 may be configured to be disposed within the ear tip at the ear canal as well. Cochlear implant 1012 and electrode lead 1014 may be configured, when implanted within the recipient, to apply electrical stimulation to the recipient. Processing unit 1004 may be communicatively coupled to acoustic receiver 1010 and cochlear implant 1012 and may be configured to perform similar operations as other implementations of system 100. For instance, processing unit 1004 may 1) direct acoustic receiver 1010 to present a sound to recipient 1006 as part of the acoustic stimulation, where the directing is configured to cause the sound to have a target sound pressure level at the ear canal; 2) obtain, by way of probe microphone 1008, a detected sound pressure level of the sound as the sound is presented at the ear canal; 3) identify a discrepancy between the detected and target sound pressure levels of the sound as the sound is presented at the ear canal; and 4) direct, based on the identified discrepancy, acoustic receiver 1010 to adjust a sound pressure level at which the sound is presented to recipient 1006 in a manner that decreases the identified discrepancy.

In this way, sound presented to recipient 1006 may be continuously calibrated as the electroacoustic hearing system is used during normal operation and issues arise to change the sound pressure level presented to recipient 1006. For example, if water partially blocks the recipient's ear canal as the recipient showers or bathes, a remedial action may be taken to automatically increase the generated sound pressure level to thereby keep the actual sound pressure level on par with the target sound pressure level. As another example, a remedial action in response to a drop in sound pressure level could include notifying recipient 1006 or a caregiver of the recipient that a decrease in sound pressure level has been detected.

Figure 11B:
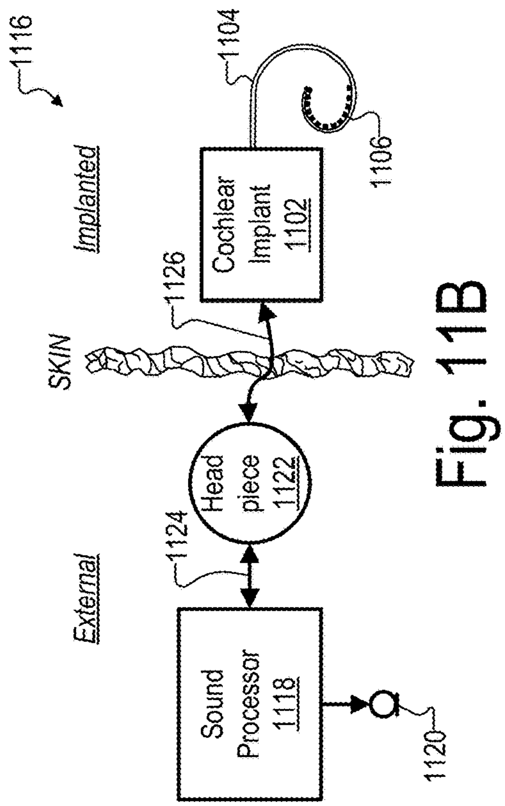
FIGS. 11A-11C shows illustrative implementations of a cochlear implant system that may be used by a recipient to whom calibrated sound is delivered in accordance with systems and methods described herein.
Figure 11C:
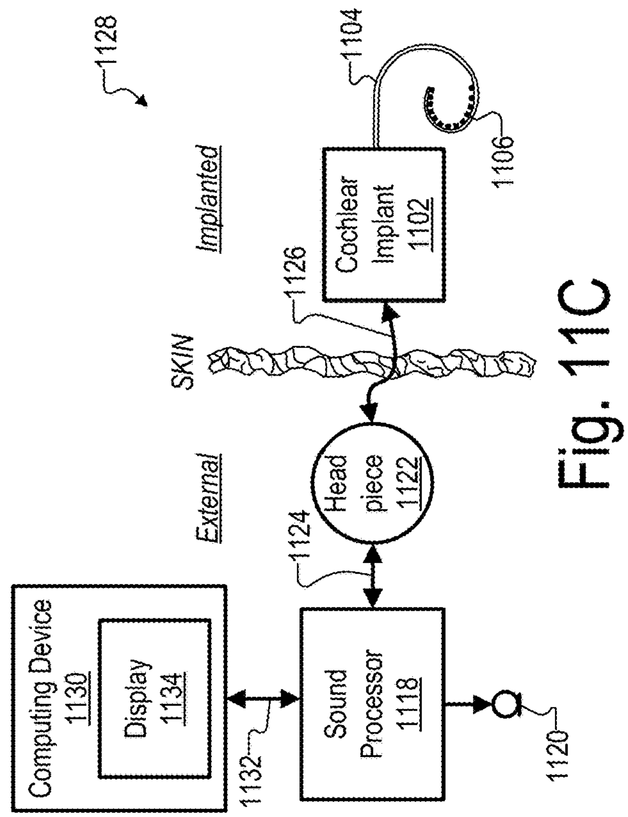
Figure 11A:
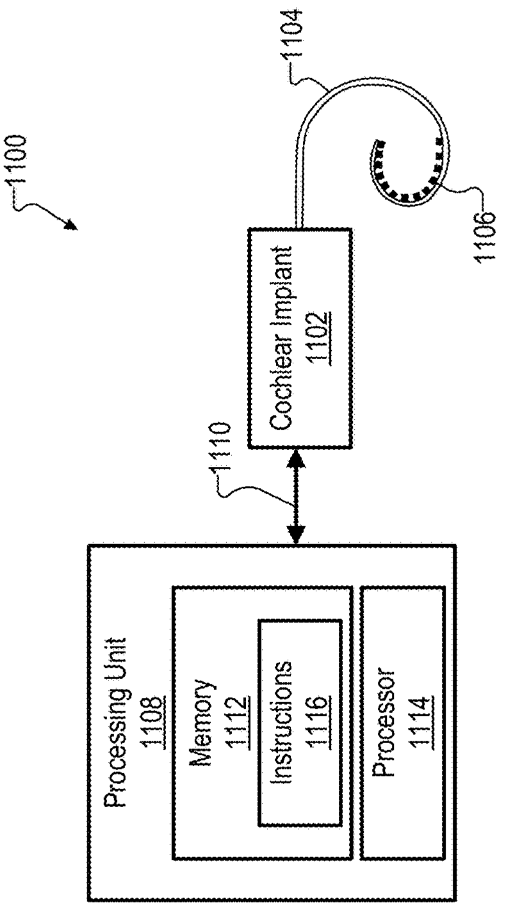

FIGS. 11A-11C shows illustrative implementations of a cochlear implant system 1100 that may be used by a recipient to whom calibrated sound is delivered in accordance with systems and methods described herein. For example, any of the cochlear implant systems mentioned above may be implemented by cochlear implant system 1100 or an implementation thereof. Cochlear implant system 1100 and implementations thereof will now be described in more detail in relation to FIGS. 11A-11C.

FIG. 11A illustrates an exemplary cochlear implant system 1100 configured to be used by a recipient. As shown, cochlear implant system 1100 includes a cochlear implant 1102, an electrode lead 1104 physically coupled to cochlear implant 1102 and having an array of electrodes 1106, and a processing unit 1108 configured to be communicatively coupled to cochlear implant 1102 by way of a communication link 1110.

The cochlear implant system 1100 shown in FIG. 11A is unilateral (i.e., associated with only one ear of the recipient). Alternatively, a bilateral configuration of cochlear implant system 1100 may include separate cochlear implants and electrode leads for each ear of the recipient. In the bilateral configuration, processing unit 1108 may be implemented by a single processing unit configured to interface with both cochlear implants or by two separate processing units each configured to interface with a different one of the cochlear implants.

Cochlear implant 1102 may be implemented by any suitable type of implantable stimulator. For example, cochlear implant 1102 may be implemented by an implantable cochlear stimulator. Additionally or alternatively, cochlear implant 1102 may be implemented by a brainstem implant and/or any other type of device that may be implanted within the recipient and configured to apply electrical stimulation to one or more stimulation sites located along an auditory pathway of the recipient.

In some examples, cochlear implant 1102 may be configured to generate electrical stimulation representative of an audio signal processed by processing unit 1108 in accordance with one or more stimulation parameters transmitted to cochlear implant 1102 by processing unit 1108. Cochlear implant 1102 may be further configured to apply the electrical stimulation to one or more stimulation sites (e.g., one or more intracochlear locations) within the recipient by way of one or more electrodes 1106 on electrode lead 1104. In some examples, cochlear implant 1102 may include a plurality of independent current sources each associated with a channel defined by one or more of electrodes 1106. In this manner, different stimulation current levels may be applied to multiple stimulation sites simultaneously by way of multiple electrodes 1106.

Cochlear implant 1102 may additionally or alternatively be configured to generate, store, and/or transmit data. For example, cochlear implant may use one or more electrodes 1106 to record one or more signals (e.g., one or more voltages, impedances, evoked responses within the recipient, and/or other measurements) and transmit, by way of communication link 1110, data representative of the one or more signals to processing unit 1108. In some examples, this data is referred to as back telemetry data.

Electrode lead 1104 may be implemented in any suitable manner. For example, a distal portion of electrode lead 1104 may be pre-curved such that electrode lead 1104 conforms with the helical shape of the cochlea after being implanted. Electrode lead 1104 may alternatively be naturally straight or of any other suitable configuration.

In some examples, electrode lead 1104 includes a plurality of wires (e.g., within an outer sheath) that conductively couple electrodes 1106 to one or more current sources within cochlear implant 1102. For example, if there are n electrodes 1106 on electrode lead 1104 and n current sources within cochlear implant 1102, there may be n separate wires within electrode lead 1104 that are configured to conductively connect each electrode 1106 to a different one of the n current sources. Exemplary values for n are 8, 12, 16, or any other suitable number.

Electrodes 1106 are located on at least a distal portion of electrode lead 1104. In this configuration, after the distal portion of electrode lead 1104 is inserted into the cochlea, electrical stimulation may be applied by way of one or more of electrodes 1106 to one or more intracochlear locations. One or more other electrodes (e.g., including a ground electrode, not explicitly shown) may also be disposed on other parts of electrode lead 1104 (e.g., on a proximal portion of electrode lead 1104) to, for example, provide a current return path for stimulation current applied by electrodes 1106 and to remain external to the cochlea after the distal portion of electrode lead 1104 is inserted into the cochlea. Additionally or alternatively, a housing of cochlear implant 1102 may serve as a ground electrode for stimulation current applied by electrodes 1106.

Processing unit 1108 may be configured to interface with (e.g., control and/or receive data from) cochlear implant 1102. For example, processing unit 1108 may transmit commands (e.g., stimulation parameters and/or other types of operating parameters in the form of data words included in a forward telemetry sequence) to cochlear implant 1102 by way of communication link 1110. Processing unit 1108 may additionally or alternatively provide operating power to cochlear implant 1102 by transmitting one or more power signals to cochlear implant 1102 by way of communication link 1110. Processing unit 1108 may additionally or alternatively receive data from cochlear implant 1102 by way of communication link 1110. Communication link 1110 may be implemented by any suitable number of wired and/or wireless bidirectional and/or unidirectional links.

As shown, processing unit 1108 includes a memory 1112 and a processor 1114 configured to be selectively and communicatively coupled to one another. In some examples, memory 1112 and processor 1114 may be distributed between multiple devices and/or multiple locations as may serve a particular implementation.

Memory 1112 may be implemented by any suitable non-transitory computer-readable medium and/or non-transitory processor-readable medium, such as any combination of non-volatile storage media and/or volatile storage media. Exemplary non-volatile storage media include, but are not limited to, read-only memory, flash memory, a solid-state drive, a magnetic storage device (e.g., a hard drive), ferroelectric random-access memory ("RAM"), and an optical disc. Exemplary volatile storage media include, but are not limited to, RAM (e.g., dynamic RAM).

Memory 1112 may maintain (e.g., store) executable data used by processor 1114 to perform one or more of the operations described herein. For example, memory 1112 may store instructions 1116 that may be executed by processor 1114 to perform any of the operations described herein. Instructions 1116 may be implemented by any suitable application, program (e.g., sound processing program), software, code, and/or other executable data instance. Memory 1112 may also maintain any data received, generated, managed, used, and/or transmitted by processor 1114.

Processor 1114 may be configured to perform (e.g., execute instructions 1116 stored in memory 1112 to perform) various operations with respect to cochlear implant 1102.

To illustrate, processor 1114 may be configured to control an operation of cochlear implant 1102. For example, processor 1114 may receive an audio signal (e.g., by way of a microphone communicatively coupled to processing unit 1108, a wireless interface (e.g., a Bluetooth interface), and/or a wired interface (e.g., an auxiliary input port)). Processor 1114 may process the audio signal in accordance with a sound processing program (e.g., a sound processing program stored in memory 1112) to generate appropriate stimulation parameters. Processor 1114 may then transmit the stimulation parameters to cochlear implant 1102 to direct cochlear implant 1102 to apply electrical stimulation representative of the audio signal to the recipient.

In some implementations, processor 1114 may also be configured to apply acoustic stimulation to the recipient. For example, in an electroacoustic hearing system implementation of cochlear implant system 1100 such as has been described, an acoustic receiver (also referred to as a loudspeaker) may be optionally coupled to processing unit 1108. In this configuration, processor 1114 may deliver acoustic stimulation to the recipient by way of the receiver. The acoustic stimulation may be representative of an audio signal (e.g., an amplified version of the audio signal), configured to elicit an evoked response within the recipient, and/or otherwise configured. In configurations in which processor 1114 is configured to both deliver acoustic stimulation to the recipient and direct cochlear implant 1102 to apply electrical stimulation to the recipient, cochlear implant system 1100 may be referred to as an electroacoustic hearing system or another suitable term.

Processor 1114 may be additionally or alternatively configured to receive and process data generated by cochlear implant 1102. For example, processor 1114 may receive data representative of a signal recorded by cochlear implant 1102 using one or more electrodes 1106 and, based on the data, adjust one or more operating parameters of processing unit 1108. Additionally or alternatively, processor 1114 may use the data to perform one or more diagnostic operations with respect to cochlear implant 1102 and/or the recipient.

Other operations may be performed by processor 1114 as may serve a particular implementation. In the description provided herein, any references to operations performed by processing unit 1108 and/or any implementation thereof may be understood to be performed by processor 1114 based on instructions 1116 stored in memory 1112.

Processing unit 1108 may be implemented by one or more devices configured to interface with cochlear implant 1102. To illustrate, FIG. 11B shows an exemplary configuration 1116 of cochlear implant system 1100 in which processing unit 1108 is implemented by a sound processor 1118 configured to be located external to the recipient. In configuration 1116, sound processor 1118 is communicatively coupled to a microphone 1120 and to a headpiece 1122 that are both configured to be located external to the recipient.

Sound processor 1118 may be implemented by any suitable device that may be worn or carried by the recipient. For example, sound processor 1118 may be implemented by a behind-the-ear ("BTE") unit configured to be worn behind and/or on top of an ear of the recipient. Additionally or alternatively, sound processor 1118 may be implemented by an off-the-ear unit (also referred to as a body worn device) configured to be worn or carried by the recipient away from the ear. Additionally or alternatively, at least a portion of sound processor 1118 is implemented by circuitry within headpiece 1122.

Microphone 1120 is configured to detect one or more audio signals (e.g., that include speech and/or any other type of sound) in an environment of the recipient. Microphone 1120 may be implemented in any suitable manner. For example, microphone 1120 may be implemented by a microphone that is configured to be placed within the concha of the ear near the entrance to the ear canal, such as a T-MIC™ microphone from Advanced Bionics. Such a microphone may be held within the concha of the ear near the entrance of the ear canal during normal operation by a boom or stalk that is attached to an ear hook configured to be selectively attached to sound processor 1118. Additionally or alternatively, microphone 1120 may be implemented by one or more microphones in or on headpiece 1122, one or more microphones in or on a housing of sound processor 1118, one or more beam-forming microphones, and/or any other suitable microphone as may serve a particular implementation. Along with microphone 1120, a probe microphone (not explicitly shown) may also be disposed in an ear tip at the ear canal to monitor sound presented to the recipient at the ear canal in accordance with principles described above.

Headpiece 1122 may be selectively and communicatively coupled to sound processor 1118 by way of a communication link 1124 (e.g., a cable or any other suitable wired or wireless communication link), which may be implemented in any suitable manner. Headpiece 1122 may include an external antenna (e.g., a coil and/or one or more wireless communication components) configured to facilitate selective wireless coupling of sound processor 1118 to cochlear implant 1102. Headpiece 1122 may additionally or alternatively be used to selectively and wirelessly couple any other external device to cochlear implant 1102. To this end, headpiece 1122 may be configured to be affixed to the recipient's head and positioned such that the external antenna housed within headpiece 1122 is communicatively coupled to a corresponding implantable antenna (which may also be implemented by a coil and/or one or more wireless communication components) included within or otherwise connected to cochlear implant 1102. In this manner, stimulation parameters and/or power signals may be wirelessly and transcutaneously transmitted between sound processor 1118 and cochlear implant 1102 by way of a wireless communication link 1126.

In configuration 1116, sound processor 1118 may receive an audio signal detected by microphone 1120 by receiving a signal (e.g., an electrical signal) representative of the audio signal from microphone 1120. Sound processor 1118 may additionally or alternatively receive the audio signal by way of any other suitable interface as described herein. Sound processor 1118 may process the audio signal in any of the ways described herein and transmit, by way of headpiece 1122, stimulation parameters to cochlear implant 1102 to direct cochlear implant 1102 to apply electrical stimulation representative of the audio signal to the recipient.

In an alternative configuration, sound processor 1118 may be implanted within the recipient instead of being located external to the recipient. In this alternative configuration, which may be referred to as a fully implantable configuration of cochlear implant system 1100, sound processor 1118 and cochlear implant 1102 may be combined into a single device or implemented as separate devices configured to communicate one with another by way of a wired and/or wireless communication link. In a fully implantable implementation of cochlear implant system 1100, headpiece 1122 may not be included and microphone 1120 may be implemented by one or more microphones implanted within the recipient, located within an ear canal of the recipient, and/or external to the recipient.

FIG. 11C shows an exemplary configuration 1128 of cochlear implant system 1100 in which processing unit 1108 is implemented by a combination of sound processor 1118 and a computing device 1130 configured to communicatively couple to sound processor 1118 by way of a communication link 1132, which may be implemented by any suitable wired or wireless communication link.

Computing device 1130 may be implemented by any suitable combination of hardware and software. To illustrate, computing device 1130 may be implemented by a mobile device (e.g., a mobile phone, a laptop, a tablet computer, etc.), a desktop computer, and/or any other suitable computing device as may serve a particular implementation. As an example, computing device 1130 may be implemented by a mobile device configured to execute an application (e.g., a "mobile app") that may be used by a user (e.g., the recipient, a clinician, and/or any other user) to control one or more settings of sound processor 1118 and/or cochlear implant 1102 and/or perform one or more operations (e.g., diagnostic operations) with respect to data generated by sound processor 1118 and/or cochlear implant 1102.

In some examples, computing device 1130 may be configured to control an operation of cochlear implant 1102 by transmitting one or more commands to cochlear implant 1102 by way of sound processor 1118. Likewise, computing device 1130 may be configured to receive data generated by cochlear implant 1102 by way of sound processor 1118. Alternatively, computing device 1130 may interface with (e.g., control and/or receive data from) cochlear implant 1102 directly by way of a wireless communication link between computing device 1130 and cochlear implant 1102. In some implementations in which computing device 1130 interfaces directly with cochlear implant 1102, sound processor 1118 may or may not be included in cochlear implant system 1100.

Computing device 1130 is shown as having an integrated display 1134. Display 1134 may be implemented by a display screen, for example, and may be configured to display content generated by computing device 1130. Additionally or alternatively, computing device 1130 may be communicatively coupled to an external display device (not shown) configured to display the content generated by computing device 1130.

In some examples, computing device 1130 represents a fitting device configured to be selectively used (e.g., by a clinician) to fit sound processor 1118 and/or cochlear implant 1102 to the recipient. In these examples, computing device 1130 may be configured to execute a fitting program configured to set one or more operating parameters of sound processor 1118 and/or cochlear implant 1102 to values that are optimized for the recipient. As such, in these examples, computing device 1130 may not be considered to be part of cochlear implant system 1100. Instead, computing device 1130 may be considered to be separate from cochlear implant system 1100 such that computing device 1130 may be selectively coupled to cochlear implant system 1100 when it is desired to fit sound processor 1118 and/or cochlear implant 1102 to the recipient.

In certain embodiments, one or more of the processes described herein may be implemented at least in part as instructions embodied in a non-transitory computer-readable medium and executable by one or more computing devices. In general, a processor (e.g., a microprocessor) receives instructions, from a non-transitory computer-readable medium, (e.g., a memory, etc.), and executes those instructions, thereby performing one or more processes, including one or more of the processes described herein. Such instructions may be stored and/or transmitted using any of a variety of known computer-readable media.

A computer-readable medium (also referred to as a processor-readable medium) includes any non-transitory medium that participates in providing data (e.g., instructions) that may be read by a computer (e.g., by a processor of a computer). Such a medium may take many forms, including, but not limited to, non-volatile media, and/or volatile media. Non-volatile media may include, for example, optical or magnetic disks and other persistent memory. Volatile media may include, for example, dynamic random access memory (DRAM), which typically constitutes a main memory. Common forms of computer-readable media include, for example, a disk, hard disk, magnetic tape, any other magnetic medium, a compact disc read-only memory (CD-ROM), a digital video disc (DVD), any other optical medium, random access memory (RAM), programmable read-only memory (PROM), electrically erasable programmable read-only memory (EPROM), FLASH-EEPROM, any other memory chip or cartridge, or any other tangible medium from which a computer can read.

Figure 12:
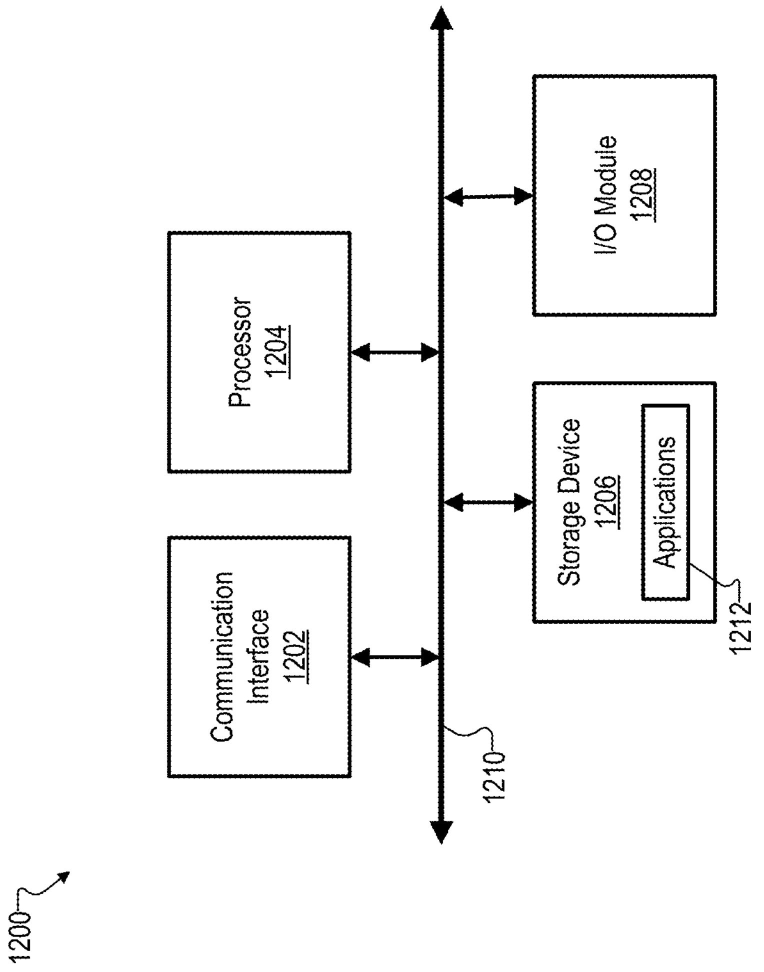
FIG. 12 shows an illustrative computing system that may implement any of the computing systems or devices described herein

FIG. 12 shows an illustrative computing device 1200 that may be specifically configured to perform one or more of the processes described herein. For example, computing system 1200 may include or implement (or partially implement) a sound calibration system such as system 100 or any component included therein or system associated therewith. In some examples, computing system 1200 may include or implement a system configuration device or implementation thereof such as system configuration device 604 of FIG. 6, insertion monitoring device 704 of FIG. 7, clinician fitting device 804 of FIG. 8, system configuration device 904 of FIG. 9, a processing unit of electroacoustic hearing system 1000 of FIG. 10, a processing unit of any of the implementations of cochlear implant system 1100 of FIGS. 11A-11C, or any other computing systems or devices described herein.

As shown in FIG. 12, computing system 1200 may include a communication interface 1202, a processor 1204, a storage device 1206, and an input/output (I/O) module 1208 communicatively connected via a communication infrastructure 1210. While an illustrative computing system 1200 is shown in FIG. 12, the components illustrated in FIG. 12 are not intended to be limiting. Additional or alternative components may be used in other embodiments. Components of computing system 1200 shown in FIG. 12 will now be described in additional detail.

Communication interface 1202 may be configured to communicate with one or more computing devices. Examples of communication interface 1202 include, without limitation, a wired network interface (such as a network interface card), a wireless network interface (such as a wireless network interface card), a modem, an audio/video connection, and any other suitable interface.

Processor 1204 generally represents any type or form of processing unit capable of processing data or interpreting, executing, and/or directing execution of one or more of the instructions, processes, and/or operations described herein. Processor 1204 may direct execution of operations in accordance with one or more applications 1212 or other computer-executable instructions such as may be stored in storage device 1206 or another computer-readable medium.

Storage device 1206 may include one or more data storage media, devices, or configurations and may employ any type, form, and combination of data storage media and/or device. For example, storage device 1206 may include, but is not limited to, a hard drive, network drive, flash drive, magnetic disc, optical disc, RAM, dynamic RAM, other non-volatile and/or volatile data storage units, or a combination or sub-combination thereof. Electronic data, including data described herein, may be temporarily and/or permanently stored in storage device 1206. For example, data representative of one or more executable applications 1212 configured to direct processor 1204 to perform any of the operations described herein may be stored within storage device 1206. In some examples, data may be arranged in one or more databases residing within storage device 1206.

I/O module 1208 may include one or more I/O modules configured to receive user input and provide user output. One or more I/O modules may be used to receive input for a single virtual experience. I/O module 1208 may include any hardware, firmware, software, or combination thereof supportive of input and output capabilities. For example, I/O module 1208 may include hardware and/or software for capturing user input, including, but not limited to, a keyboard or keypad, a touchscreen component (e.g., touchscreen display), a receiver (e.g., an RF or infrared receiver), motion sensors, and/or one or more input buttons.

I/O module 1208 may include one or more devices for presenting output to a user, including, but not limited to, a graphics engine, a display (e.g., a display screen), one or more output drivers (e.g., display drivers), one or more audio speakers, and one or more audio drivers. In certain embodiments, I/O module 1208 is configured to provide graphical data to a display for presentation to a user. The graphical data may be representative of one or more graphical user interfaces and/or any other graphical content as may serve a particular implementation.

In some examples, any of the facilities described herein may be implemented by or within one or more components of computing system 1200. For example, one or more applications 1212 residing within storage device 1206 may be configured to direct processor 1204 to perform one or more processes or functions associated with processor 104 of system 100. Likewise, memory 102 of system 100 may be implemented by or within storage device 1206.

In the preceding description, various illustrative embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. An electroacoustic hearing system comprising:

a loudspeaker; and a processor configured to:

direct the loudspeaker to present a sound to a recipient by way of a length of tubing extending from the loudspeaker to an ear tip disposed at an ear canal of the recipient, the directing configured to cause the sound to have a target sound pressure level at the ear canal;

obtain a detected sound pressure level of the sound as the sound is presented at the ear canal, the detected sound pressure level obtained from a probe microphone disposed within the ear tip;

identify a discrepancy between the detected and target sound pressure levels of the sound as the sound is presented at the ear canal; and direct, based on the identified discrepancy, a remedial action to be performed to compensate for the discrepancy.

2. The electroacoustic hearing system of claim 1, wherein:

the recipient is a recipient of a cochlear implant system that includes a cochlear implant and an electrode lead that are implanted within the recipient during a surgical insertion procedure; and the loudspeaker is included within an insertion monitoring device configured to evoke and measure electrocochleographic (ECochG) potentials produced by the recipient as the surgical insertion procedure is performed.

3. The electroacoustic hearing system of claim 1, wherein:

the electroacoustic hearing system is fitted to the recipient by a clinician during a fitting session; and the loudspeaker is included within a clinician fitting device configured to evoke and measure electrocochleographic (ECochG) potentials produced by the recipient as the fitting session is performed.

4. The electroacoustic hearing system of claim 1, wherein:

the electroacoustic hearing system includes:

a cochlear implant having an electrode lead configured, when implanted within the recipient, to apply electrical stimulation to the recipient during normal operation of the electroacoustic hearing system; and the loudspeaker is implemented by an acoustic receiver and the sound presented by the loudspeaker is implemented by acoustic stimulation applied by the acoustic receiver to the recipient during the normal operation of the electroacoustic hearing system.

5. The electroacoustic hearing system of claim 1, wherein:

the electroacoustic hearing system is set up for the recipient during a system configuration session comprising at least one of a surgical insertion procedure or a fitting session;

the loudspeaker is included within a system configuration device configured to evoke and measure electrocochleographic (ECochG) potentials produced by the recipient during the system configuration session;

the processor is further configured to obtain electroencephalogram (EEG) test results from an EEG test performed with respect to the recipient during the system configuration session; and the identifying of the discrepancy between the detected and target sound pressure levels is performed based on the EEG test results.

6. The electroacoustic hearing system of claim 1, wherein the directing of the remedial action includes directing a user to resolve an unanticipated effect associated with one or more of the loudspeaker, the length of tubing, or the ear tip.

7. The electroacoustic hearing system of claim 1, wherein the directing of the remedial action includes directing the loudspeaker to adjust a sound pressure level at which the sound is presented to the recipient in a manner that decreases the discrepancy between the detected and target sound pressure levels.

8. The electroacoustic hearing system of claim 1, wherein:

the electroacoustic hearing system is set up for the recipient during a system configuration session comprising at least one of a surgical insertion procedure or a fitting session;

the loudspeaker is included within a system configuration device configured to evoke and measure electrocochleographic (ECochG) potentials produced by the recipient during the system configuration session; and the directing of the remedial action includes directing the system configuration device to account for the discrepancy between the detected and target sound pressure levels in an analysis of the measured ECochG potentials.

9. The electroacoustic hearing system of claim 1, wherein:

the processor is further configured to continuously monitor the sound pressure level of the sound as the sound is presented at the ear canal; and the obtaining of the detected sound pressure level is performed as part of the continuous monitoring of the sound pressure level.

10. The electroacoustic hearing system of claim 1, wherein:

the length of tubing carries the sound to the recipient by way of a first channel of the ear tip;

the probe microphone detects the sound pressure level of the sound by way of a second channel of the ear tip; and the first and second channels of the ear tip are physically separate channels within the ear tip.

11. The electroacoustic hearing system of claim 10, wherein:

the first channel has an approximately circular cross section having a first radius;

the second channel has an approximately circular cross section having a second radius less than the first radius; and the second channel is disposed outside of the first channel such that the cross section of the second channel is immediately adjacent to the cross section of the first channel.

12. The electroacoustic hearing system of claim 10, wherein:

the first channel has an approximately circular cross section having a first radius;

the second channel has an approximately circular cross section having a second radius less than the first radius; and the second channel is disposed within the first channel such that the cross section of the second channel is contained within the cross section of the first channel.

13. A method comprising:

directing, by a sound calibration system, a loudspeaker of an electroacoustic hearing system to present a sound to an recipient by way of a an ear tip disposed at an ear canal of the recipient, the directing configured to cause the sound to have a target sound pressure level at the ear canal;

obtaining, by the sound calibration system from a probe microphone disposed within the ear tip, a detected sound pressure level of the sound as the sound is presented at the ear canal;

identifying, by the sound calibration system, a discrepancy between the detected and target sound pressure levels of the sound as the sound is presented at the ear canal; and directing, by the sound calibration system based on the identified discrepancy, a remedial action to be performed to compensate for the discrepancy.

14. The method of claim 13, wherein:

the recipient is a recipient of a cochlear implant system that includes a cochlear implant and an electrode lead that are implanted within the recipient during a surgical insertion procedure; and the loudspeaker is included within an insertion monitoring device configured to evoke and measure electrocochleographic (ECochG) potentials produced by the recipient as the surgical insertion procedure is performed.

15. The method of claim 13, wherein:

the electroacoustic hearing system is fitted to the recipient by a clinician during a fitting session; and the loudspeaker is included within a clinician fitting device configured to evoke and measure electrocochleographic (ECochG) potentials produced by the recipient as the fitting session is performed.

16. The method of claim 13, wherein:

the electroacoustic hearing system is set up for the recipient during a system configuration session comprising at least one of a surgical insertion procedure or a fitting session;

the loudspeaker is included within a system configuration device configured to evoke and measure electrocochleographic (ECochG) potentials produced by the recipient during the system configuration session;

the method further includes obtaining, by the sound calibration system, electroencephalogram (EEG) test results from an EEG test performed with respect to the recipient during the system configuration session; and the identifying of the discrepancy between the detected and target sound pressure levels is performed based on the EEG test results.

17. The method of claim 13, wherein the directing of the remedial action includes directing a user to resolve an unanticipated effect associated with one or more of the loudspeaker or the ear tip.

18. The method of claim 13, wherein the directing of the remedial action includes directing the loudspeaker to adjust a sound pressure level at which the sound is presented to the recipient in a manner that decreases the discrepancy between the detected and target sound pressure levels.

19. The method of claim 13, wherein:

the electroacoustic hearing system is set up for the recipient during a system configuration session comprising at least one of a surgical insertion procedure or a fitting session;

the loudspeaker is included within a system configuration device configured to evoke and measure electrocochleographic (ECochG) potentials produced by the recipient during the system configuration session; and the directing of the remedial action includes directing the system configuration device to account for the discrepancy between the detected and target sound pressure levels in an analysis of the measured ECochG potentials.

* * * * *